US007825120B2

(12) United States Patent
Morgan et al.

(10) Patent No.: US 7,825,120 B2
(45) Date of Patent: *Nov. 2, 2010

(54) CERTAIN SUBSTITUTED ((PIPERAZIN-1-YLMETHYL)BENZYL)UREAS

(75) Inventors: Bradley P. Morgan, Moraga, CA (US);
Alex Muci, San Francisco, CA (US);
Erica A. Kraynack, Belmont, CA (US);
Todd Tochimoto, Foster City, CA (US);
Pu-Ping Lu, Foster City, CA (US);
David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 11/639,398

(22) Filed: Dec. 13, 2006

(65) Prior Publication Data
US 2007/0197504 A1 Aug. 23, 2007

Related U.S. Application Data

(60) Provisional application No. 60/750,986, filed on Dec. 15, 2005.

(51) Int. Cl.
*A61K 31/497* (2006.01)
*C07D 241/04* (2006.01)
*C07D 295/00* (2006.01)

(52) U.S. Cl. .................. 514/252.12; 544/358; 424/40; 424/401; 424/408; 424/449; 424/451; 424/455; 424/456; 424/464; 424/488

(58) Field of Classification Search .................. None
See application file for complete search history.

(56) References Cited

U.S. PATENT DOCUMENTS

| | | | |
|---|---|---|---|
| 3,786,058 A | 1/1974 | Edwards | |
| 3,907,782 A | 9/1975 | Edwards | |
| 3,939,169 A | 2/1976 | Edwards | |
| 4,672,066 A | 6/1987 | Carson et al. | |
| 4,787,931 A | 11/1988 | Henrie, II et al. | |
| 5,162,360 A | 11/1992 | Creswell et al. | |
| 5,547,966 A | 8/1996 | Atwal et al. | |
| 5,556,969 A | 9/1996 | Chambers et al. | |
| 5,624,937 A | 4/1997 | Reel et al. | |
| 5,739,144 A | 4/1998 | Warrellow et al. | |
| 5,919,811 A | 7/1999 | Conti et al. | |
| 5,962,483 A | 10/1999 | Warrellow et al. | |
| 5,972,975 A | 10/1999 | Esser et al. | |
| 5,994,368 A | 11/1999 | Oku et al. | |
| 6,001,860 A | 12/1999 | Hamanaka | |
| 6,005,008 A | 12/1999 | Widdowson et al. | |
| 6,174,905 B1 | 1/2001 | Suzuki et al. | |
| 6,207,809 B1 | 3/2001 | Nestler | |
| 6,262,083 B1 | 7/2001 | Moon et al. | |
| 6,329,395 B1 | 12/2001 | Dugar et al. | |
| 6,407,124 B1 | 6/2002 | Rawlins et al. | |
| 6,573,264 B1 | 6/2003 | Zablocki et al. | |
| 6,583,282 B1 | 6/2003 | Zhang et al. | |
| 6,635,641 B2 | 10/2003 | Bender et al. | |
| 6,645,990 B2 | 11/2003 | Askew et al. | |
| 6,656,971 B2 | 12/2003 | Wu et al. | |
| 6,670,376 B1 | 12/2003 | Moran et al. | |
| 6,696,576 B2 | 2/2004 | Baumann et al. | |
| 6,916,814 B2 | 7/2005 | Moss et al. | |
| 7,176,222 B2 | 2/2007 | Morgan et al. | |
| 7,371,871 B2 * | 5/2008 | Schilling et al. | 548/346.1 |
| 7,399,866 B2 | 7/2008 | Morgan et al. | |
| 7,491,826 B2 | 2/2009 | Morgan et al. | |
| 7,507,735 B2 * | 3/2009 | Morgan et al. | 514/252.13 |
| 7,538,223 B2 | 5/2009 | Morgan et al. | |
| 2002/0165394 A1 | 11/2002 | Dumas et al. | |
| 2003/0045552 A1 | 3/2003 | Robarge et al. | |
| 2003/0096841 A1 | 5/2003 | Robarge et al. | |
| 2003/0207872 A1 | 11/2003 | Riedl et al. | |
| 2003/0229066 A1 | 12/2003 | Hendrix et al. | |
| 2003/0236287 A1 | 12/2003 | Piotrowski et al. | |
| 2004/0019099 A1 | 1/2004 | Aslanian et al. | |
| 2004/0038962 A1 | 2/2004 | Ashworth et al. | |
| 2004/0097483 A1 | 5/2004 | Zeng et al. | |
| 2004/0224875 A1 * | 11/2004 | Schilling et al. | 514/2 |
| 2004/0229937 A1 | 11/2004 | Dumas et al. | |

(Continued)

FOREIGN PATENT DOCUMENTS

DE 3147879 6/1983

(Continued)

OTHER PUBLICATIONS

Tanaka et al. Journal of Medicinal Chemistry, 1998, 41, 2390-2410.*
Patani et al. Chemical Reviews, 1996, 41(8), 3147-76.*
Trivedi et al. Journal of Medicinal Chemistry, 1994, 37(11), 1652-1659.*
International Search Report and Written Opinion mailed Jan. 14, 2005, for Application No. PCT/US04/01069, filed Jan. 14, 2004.
International Search Report and Written Opinion for International Application No. PCT/US05/21100, mailed Aug. 2, 2006, 10 pages.
Office Action mailed Jun. 22, 2006, for U.S. Appl. No. 11/032,227, filed Jan. 11, 2005.

(Continued)

*Primary Examiner*—James O Wilson
*Assistant Examiner*—Noble Jarrell
(74) *Attorney, Agent, or Firm*—Finnegan, Henderson, Farabow, Garrett & Dunner, LLP

(57) ABSTRACT

Certain substituted ((piperazin-1-ylmethyl)benzyl)urea derivatives selectively modulate the cardiac sarcomere, for example by potentiating cardiac myosin, and may be useful in the treatment of systolic heart failure including congestive heart failure.

3 Claims, No Drawings

U.S. PATENT DOCUMENTS

| | | | |
|---|---|---|---|
| 2004/0235829 A1 | 11/2004 | Scott et al. | |
| 2005/0032798 A1 | 2/2005 | Boyer et al. | |
| 2005/0038031 A1 | 2/2005 | Dumas et al. | |
| 2005/0059703 A1 | 3/2005 | Wilhelm et al. | |
| 2005/0159416 A1 | 7/2005 | Morgan et al. | |
| 2006/0014761 A1 | 1/2006 | Morgan et al. | |
| 2006/0025470 A1 | 2/2006 | Morgan et al. | |
| 2006/0241110 A1 | 10/2006 | Morgan et al. | |
| 2007/0066626 A1 | 3/2007 | Morgan et al. | |
| 2007/0161617 A1 | 7/2007 | Morgan et al. | |
| 2007/0197497 A1 | 8/2007 | Morgan et al. | |
| 2007/0197504 A1 | 8/2007 | Morgan et al. | |
| 2007/0197505 A1 | 8/2007 | Morgan et al. | |
| 2007/0197507 A1 | 8/2007 | Morgan et al. | |
| 2007/0208000 A1* | 9/2007 | Morgan et al. | 514/212.01 |
| 2009/0036447 A1 | 2/2009 | Morgan et al. | |
| 2009/0099198 A1* | 4/2009 | Morgan et al. | 514/253.01 |

FOREIGN PATENT DOCUMENTS

| | | |
|---|---|---|
| EP | 27965 | 5/1981 |
| EP | 81142 | 6/1983 |
| EP | 0656350 A | 6/1995 |
| GB | 921682 | 3/1963 |
| JP | 10-168079 | 6/1998 |
| JP | 11-302173 | 11/1999 |
| JP | 2000-256194 | 9/2000 |
| JP | 2002-220338 | 8/2002 |
| NZ | 240935 | 11/1994 |
| WO | WO 84/03884 A1 | 10/1984 |
| WO | WO 92/10468 | 6/1992 |
| WO | WO 93/14074 A1 | 7/1993 |
| WO | WO 96/10559 A1 | 4/1996 |
| WO | WO 98/35941 A1 | 8/1998 |
| WO | WO 98/41510 A1 | 9/1998 |
| WO | WO 98/50346 A2 | 11/1998 |
| WO | WO 98/52558 A1 | 11/1998 |
| WO | WO 98/52559 A1 | 11/1998 |
| WO | WO 99/32106 | 7/1999 |
| WO | WO 99/32111 | 7/1999 |
| WO | WO 99/32436 A1 | 7/1999 |
| WO | WO 99/32463 A1 | 7/1999 |
| WO | WO 99/64394 A1 | 12/1999 |
| WO | WO 00/41698 | 7/2000 |
| WO | WO 01/07411 A1 | 2/2001 |
| WO | WO 01/25190 A1 | 4/2001 |
| WO | WO 01/53274 A1 | 7/2001 |
| WO | WO 02/00626 A1 | 1/2002 |
| WO | WO 02/00632 A1 | 1/2002 |
| WO | WO 02/06246 A1 | 1/2002 |
| WO | WO 02/14311 A2 | 2/2002 |
| WO | WO 02/059106 A1 | 8/2002 |
| WO | WO 02/062763 | 8/2002 |
| WO | WO 02/064576 A1 | 8/2002 |
| WO | WO 02/070462 A1 | 9/2002 |
| WO | WO 02/085857 A2 | 10/2002 |
| WO | WO 02/092576 A1 | 11/2002 |
| WO | WO 03/007942 A1 | 1/2003 |
| WO | WO 03/013523 A1 | 2/2003 |
| WO | WO 03/022820 A1 | 3/2003 |
| WO | WO 03/024933 A1 | 3/2003 |
| WO | WO 03/042164 A1 | 5/2003 |
| WO | WO 03/059258 | 7/2003 |
| WO | WO 03/062224 A1 | 7/2003 |
| WO | WO 03/062235 A1 | 7/2003 |
| WO | WO 03/072098 A1 | 9/2003 |
| WO | WO 03/074501 A1 | 9/2003 |
| WO | WO 03/082278 A1 | 10/2003 |
| WO | WO 03/082808 A1 | 10/2003 |
| WO | WO 03/082861 A2 | 10/2003 |
| WO | WO 03/088967 A1 | 10/2003 |
| WO | WO 03/091229 A1 | 11/2003 |
| WO | WO 03/093250 A2 | 11/2003 |
| WO | WO 03/097576 A2 | 11/2003 |
| WO | WO 2004/000831 A1 | 12/2003 |
| WO | WO 2004/002481 A1 | 1/2004 |
| WO | WO 2004/013102 A1 | 2/2004 |
| WO | WO 2004/013132 A1 | 2/2004 |
| WO | WO 2004/019958 A1 | 3/2004 |
| WO | WO 2004/024729 A1 | 3/2004 |
| WO | WO2004022561 * | 3/2004 |
| WO | WO 2004/039306 A2 | 5/2004 |
| WO | WO 2004/101529 A1 | 11/2004 |
| WO | WO 2007/070626 | 6/2007 |

OTHER PUBLICATIONS

Notice of Allowance and Notice of Allowability mailed Oct. 18, 2006, for U.S. Appl. No. 11/032,227, filed Jan. 11, 2005.

Office Action mailed May 29, 2007, for U.S. Appl. No. 10/890,829, filed Jul. 14, 2004.

Jeffcoat et al., STN Accession Number: 1977:462295; Document No. 87:62295 (1977).

Kempter et al., STN Accession Number: 1984:510849; Document No. 101:110849 (1983).

El-Sharief et al., STN Accession Number: 1987:549199; Document No. 107:14919 (1987).

Office Action mailed Sep. 13, 2007, for U.S. Appl. No. 10/890,829, filed Jul. 14, 2004.

Office Action mailed Sep. 7, 2007, for U.S. Appl. No. 10/541,596, filed Apr. 25, 2006.

Notice of Allowance and Notice of Allowability mailed Jan. 15, 2008, for U.S. Appl. No. 10/890,829, filed Jul. 14, 2004.

Notice of Allowance mailed Dec. 21, 2007, for U.S. Appl. No. 10/541,596, filed Apr. 25, 2006.

Supplementary Partial European Search Report completed Aug. 13, 2007 for European Application No. 04702228.

Office Action mailed Mar. 20, 2008 for U.S. Appl. No. 11/498,986, filed Aug. 4, 2006.

Examiner Search Strategy and Results mailed Mar. 20, 2008 for U.S. Appl. No. 11/498,986, filed Aug. 4, 2006

Office Action mailed Oct. 12, 2007 for U.S. Appl. No. 11/155,940, filed Jun. 16, 2005.

Jeffcoat et al.,Drug Metabolism and Disposition 5(2):157-166.

Mizukura et al., STN Accession No. 113:106314; Original Reference No. 113:17823a,17826a (1990).

Office Action mailed May 22, 2008, for U.S. Appl. No. 10/890,829, filed Jul. 14, 2004.

Notice of Allowance mailed Aug. 11, 2008 for U.S. Appl. No. 11/155,940, filed Jun. 16, 2005.

Office Action mailed Jul. 10, 2008 for U.S. Appl. No. 11/640,438, filed Dec. 14, 2006.

International Search Report and Written Opinion for International Application No. PCT/US2006/047976 mailed Sep. 23, 2008 (10 pages).

Office Action mailed Aug. 28, 2008 for U.S. Appl. No. 11/498,986, filed Aug. 4, 2006.

International Search Report and Written Opinion for International Application No. PCT/US2006/047827 mailed Sep. 22, 2008 (10 pages).

International Search Report and Written Opinion for International Application No. PCT/US2006/047680 mailed Sep. 24, 2008 (10 pages).

Notice of Allowance and Notice of Allowability mailed Jan. 15, 2008, for U.S. Appl. No. 10/890,829, filed Jul. 14, 2004.

Office Action mailed Oct. 15, 2008, for U.S. Appl. No. 11/639,400, filed Dec. 13, 2006.

Office Action mailed Sep. 4, 2008, for U.S. Appl. No. 11/639,390, filed Dec. 13, 2006.

Notice of Allowability mailed Nov. 28, 2008 for U.S. Appl. No. 11/498,986, filed Aug. 4, 2006.

Notice of Allowance dated Sep. 29, 2008 for U.S. Appl. No. 10/890,829, filed Jul. 14, 2004.

Final Office Action dated May 20, 2008 for U.S. Appl. No. 11/155,940, filed Jun. 16, 2005.

Office Action dated Mar. 5, 2009 for U.S. Appl. No. 11/639,380, filed Dec. 13, 2006.

Office Action dated Aug. 6, 2009 for U.S. Appl. No. 11/639,380, filed Dec. 13, 2006.

Office Action dated Mar. 3, 2009 for U.S. Appl. No. 11/639,390, filed Dec. 13, 2006.

Office Action dated Aug. 5, 2009 for U.S. Appl. No. 11/639,390, filed Dec. 13, 2006.

Notice of Allowance dated Jan. 8, 2010 for U.S. Appl. No. 11/639,390, filed Dec. 13, 2006.

Office Action dated Jan. 6, 2009 for U.S. Appl. No. 11/640,438, field Dec. 14, 2006.

International Search Report and Written Opinion mailed Feb. 27, 2008 for International Application No. PCT/US2006/047672, international filing date Dec. 14, 2006.

International Search Report and Written Opinion mailed Jan. 29, 2009 for International Application No. PCT/US2006/047668, international filing date Dec. 13, 2006.

Aslanian et al., 2002, "Identification of a Novel, Orally Bioavailable Histamine $H_3$ Receptor Antagonist Based on the 4-Benzyl-(1 H-imidazol-4-yl) Template," Bioorganic & Medicinal Chemistry Letters, 12(6): 937-941.

Di Fabio et al., 1999, "Substituted Analogues of GV150526 as Potent Glycine Binding Site Antagonists in Animal Models of Cerebral Ischemia," J. Med. Chem., 42(18): 3486-3493.

Fehr et al., 1974, "Antihypertensiv wirksame Harnstoffderivate des 8β-Aminomethyl-6-methyl-ergolens, 78. Mitteilung über Mutterkornalkaloide (1)," Eur. J. Med. Chem.—Chimica Therapeutica, 9(6): 597-601.

Henrie II et al., 1988, "Activity Optimization of Pyridinyl N-Oxidase Urea Cytokinin Mimics," J. Agric. Food Chem., 36(3): 626-633.

Jones et al., 1968, "Amidines and Guanidines Related to Congocidin. Part IV. Thiophen, Pyridine, and Benzene Analogues," J. Chem. Soc. (C), (5): 550-554.

Koščík et al., 1987, "Synthesis and addition-nucleophilic reactions of 2-chloro- and 2,6-dimethyl-4-chloro-3-pyridyl isocyanates," Chem. Papers, 41(5): 683-691.

Kujundžić et al., 1991, "Synthesis of 8-Methyl-1,2,3,4-tetrahydropyrido-[3,4-d]pyrimidine-2,4-diones," Croatica Chemica Acta, 64(4): 599-606.

Mamouni et al., 2003, "A Facile Synthesis of New 3-Substituted-2,3-dihydropyrido[3,2-d]pyrimidine-2,4-diones," Synthetic Communications, 33(24): 4259-4268.

Schoene et al., 1976, "Protective Activity of Pyridinium Salts Against Soman Poisoning In Vivo and In Vitro," Biochemical Pharmacology, 25(17): 1955-1958.

Vinkers et al., 2003, "Synopsis: SYNthesize and OPtimize System in Silico," J. med. Chem., 46(13): 2765-2773.

Registry Records Not Indexed in Chemical Abstacts (10 records total) (5 pages), July 21, 2004.

El-Sarief et al., STN Accession No. 1987:549199; Document No. 107:14919 (1987).

\* cited by examiner

CERTAIN SUBSTITUTED ((PIPERAZIN-1-YLMETHYL)BENZYL)UREAS

This application claims the benefit of U.S. provisional patent application No. 60/750,986, filed 15 Dec. 2005, which is incorporated herein by reference.

The invention relates to certain substituted urea derivatives, particularly to certain chemical entities that selectively modulate the cardiac sarcomere, and specifically to certain chemical entities, pharmaceutical compositions and methods for treating heart disease.

The "sarcomere" is an elegantly organized cellular structure found in cardiac and skeletal muscle made up of interdigitating thin and thick filaments; it comprises nearly 60% of cardiac cell volume. The thick filaments are composed of "myosin," the protein responsible for transducing chemical energy (ATP hydrolysis) into force and directed movement. Myosin and its functionally related cousins are called motor proteins. The thin filaments are composed of a complex of proteins. One of these proteins, "actin" (a filamentous polymer) is the substrate upon which myosin pulls during force generation. Bound to actin are a set of regulatory proteins, the "troponin complex" and "tropomyosin," which make the actin-myosin interaction dependent on changes in intracellular $Ca^{2+}$ levels. With each heartbeat, $Ca^{2+}$ levels rise and fall, initiating cardiac muscle contraction and then cardiac muscle relaxation. Each of the components of the sarcomere contributes to its contractile response.

Myosin is the most extensively studied of all the motor proteins. Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II consists of two globular head domains linked together by a long alpha-helical coiled-coiled tail that assembles with other myosin-IIs to form the core of the sarcomere's thick filament. The globular heads have a catalytic domain where the actin binding and ATP functions of myosin take place. Once bound to an actin filament, the release of phosphate (cf. ATP to ADP) leads to a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound. Un-binding of the globular head from the actin filament (also $Ca^{2+}$ modulated) coupled with return of the catalytic domain and light chain to their starting conformation/orientation completes the contraction and relaxation cycle.

Mammalian heart muscle consists of two forms of cardiac myosin, alpha and beta, and they are well characterized. The beta form is the predominant form (>90 percent) in adult human cardiac muscle. Both have been observed to be regulated in human heart failure conditions at both transcriptional and translational levels, with the alpha form being down-regulated in heart failure.

The sequences of all of the human skeletal, cardiac, and smooth muscle myosins have been determined. While the cardiac alpha and beta myosins are very similar (93% identity), they are both considerably different from human smooth muscle (42% identity) and more closely related to skeletal myosins (80% identity). Conveniently, cardiac muscle myosins are incredibly conserved across mammalian species. For example, both alpha and beta cardiac myosins are >96% conserved between humans and rats, and the available 250-residue sequence of porcine cardiac beta myosin is 100% conserved with the corresponding human cardiac beta myosin sequence. Such sequence conservation contributes to the predictability of studying myosin based therapeutics in animal based models of heart failure.

The components of the cardiac sarcomere present targets for the treatment of heart failure, for example by increasing contractility or facilitating complete relaxation to modulate systolic and diastolic function, respectively.

Congestive heart failure ("CHF") is not a specific disease, but rather a constellation of signs and symptoms, all of which are caused by an inability of the heart to adequately respond to exertion by increasing cardiac output. The dominant pathophysiology associated with CHF is systolic dysfunction, an impairment of cardiac contractility (with a consequent reduction in the amount of blood ejected with each heartbeat). Systolic dysfunction with compensatory dilation of the ventricular cavities results in the most common form of heart failure, "dilated cardiomyopathy," which is often considered to be one in the same as CHF. The counterpoint to systolic dysfunction is diastolic dysfunction, an impairment of the ability to fill the ventricles with blood, which can also result in heart failure even with preserved left ventricular function. Congestive heart failure is ultimately associated with improper function of the cardiac myocyte itself, involving a decrease in its ability to contract and relax.

Many of the same underlying conditions can give rise to systolic and/or diastolic dysfunction, such as atherosclerosis, hypertension, viral infection, valvular dysfunction, and genetic disorders. Patients with these conditions typically present with the same classical symptoms: shortness of breath, edema and overwhelming fatigue. In approximately half of the patients with dilated cardiomyopathy, the cause of their heart dysfunction is ischemic heart disease due to coronary atherosclerosis. These patients have had either a single myocardial infarction or multiple myocardial infarctions; here, the consequent scarring and remodeling results in the development of a dilated and hypocontractile heart. At times the causative agent cannot be identified, so the disease is referred to as "idiopathic dilated cardiomyopathy." Irrespective of ischemic or other origin, patients with dilated cardiomyopathy share an abysmal prognosis, excessive morbidity and high mortality.

The prevalence of CHF has grown to epidemic proportions as the population ages and as cardiologists have become more successful at reducing mortality from ischemic heart disease, the most common prelude to CHF. Roughly 4.6 million people in the United States have been diagnosed with CHF; the incidence of such diagnosis is approaching 10 per 1000 after 65 years of age. Hospitalization for CHF is usually the result of inadequate outpatient therapy. Hospital discharges for CHF rose from 377,000 (in 1979) to 970,000 (in 2002) making CHF the most common discharge diagnosis in people age 65 and over. The five-year mortality from CHF approaches 50%. Hence, while therapies for heart disease have greatly improved and life expectancies have extended over the last several years, new and better therapies continue to be sought, for example, for CHF.

"Acute" congestive heart failure (also known as acute "decompensated" heart failure) involves a precipitous drop in cardiac function resulting from a variety of causes. For example in a patient who already has congestive heart failure, a new myocardial infarction, discontinuation of medications, and dietary indiscretions may all lead to accumulation of edema fluid and metabolic insufficiency even in the resting state. A therapeutic agent that increases cardiac function during such an acute episode could assist in relieving this metabolic insufficiency and speeding the removal of edema, facilitating the return to the more stable "compensated" congestive heart failure state. Patients with very advanced congestive heart failure particularly those at the end stage of the disease also could benefit from a therapeutic agent that increases cardiac function, for example, for stabilization while waiting for a heart transplant. Other potential benefits could be provided to patients coming off a bypass pump, for example, by administration of an agent that assists the stopped or slowed heart in resuming normal function. Patients who have diastolic dysfunction (insufficient relaxation of the heart muscle) could benefit from a therapeutic agent that modulates relaxation.

Inotropes are drugs that increase the contractile ability of the heart. As a group, all current inotropes have failed to meet the gold standard for heart failure therapy, i.e., to prolong patient survival. In addition, current agents are poorly selective for cardiac tissue, in part leading to recognized adverse effects that limit their use. Despite this fact, intravenous inotropes continue to be widely used in acute heart failure (e.g., to allow for reinstitution of oral medications or to bridge patients to heart transplantation) whereas in chronic heart failure, orally given digoxin is used as an inotrope to relieve patient symptoms, improve the quality of life, and reduce hospital admissions.

Given the limitations of current agents, new approaches are needed to improve cardiac function in congestive heart failure. The most recently approved short-term intravenous agent, milrinone, is now nearly fifteen years old. The only available oral drug, digoxin, is over 200 hundred years old. There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes.

Current inotropic therapies improve contractility by increasing the calcium transient via the adenylyl cyclase pathway, or by delaying cAMP degradation through inhibition of phosphodiesterase (PDE), which can be detrimental to patients with heart failure.

Given the limitations of current agents, new approaches are needed to improve cardiac function in congestive heart failure. The most recently approved short-term intravenous agent, milrinone, is more than fifteen years old. The only available oral drug, digoxin, is over 200 hundred years old. There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes.

The selectivity of agents directed at the cardiac sarcomere (for example, by targeting cardiac beta myosin) has been identified as an important means to achieve this improved therapeutic index. The present invention provides such agents (particularly sarcomere activating agents) and methods for their identification and use.

Another approach may be to directly activate cardiac myosin without changing the calcium transient to improving cardiac contractility. The present invention provides such agents (particularly myosin activating agents) and methods for their identification and use.

The present invention provides chemical entities, pharmaceutical compositions and methods for the treatment of heart failure including CHF, particularly systolic heart failure. The compositions are selective modulators of the cardiac sarcomere, for example, potentiating cardiac myosin.

The present invention provides at least one chemical entity chosen from compounds of Formula I

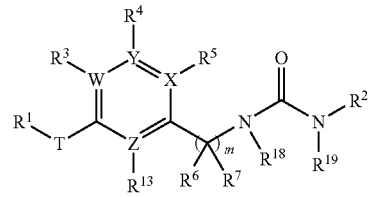

and pharmaceutically acceptable salts, solvates, chelates, non-covalent complexes, prodrugs, and mixtures thereof, wherein W, X, Y and Z are chosen from —CH= and —N=, provided that no more than two of W, X Y and Z are —N=;

T is selected from a bond, optionally substituted lower alkylene, —O—, —O-(optionally substituted lower alkylene)-, -(optionally substituted lower alkylene)-O—, —S—, —S-(optionally substituted lower alkylene)-, -(optionally substituted lower alkylene)-S—, —SO$_2$—, —SO$_2$-(optionally substituted lower alkylene)-, and -(optionally substituted lower alkylene)-SO$_2$—;

$R^{18}$ and $R^{19}$ are independently selected from hydrogen, optionally substituted alkyl, optionally substituted cycloalkyl, optionally substituted heteroalkyl, optionally substituted heterocycloalkyl, optionally substituted aryl and optionally substituted heteroaryl;

$R^1$ is chosen from optionally substituted alkyl, optionally substituted amino, optionally substituted aryl, optionally substituted heteroaryl, optionally substituted cycloalkyl and optionally substituted heterocycloalkyl;

$R^2$ is chosen from optionally substituted aryl, optionally substituted aralkyl; optionally substituted cycloalkyl, optionally substituted heteroaryl, optionally substituted heteroaralkyl and optionally substituted heterocycloalkyl;

$R^3$, $R^4$, $R^5$, and $R^{13}$ are independently chosen from hydrogen, halo, cyano, optionally substituted alkyl, optionally substituted alkoxy, optionally substituted heterocycloalkyl, and optionally substituted heteroaryl, provided that when W is —N= then $R^3$ is absent, when Y is —N= then $R^4$ is absent, when X is —N= then $R^5$ is absent, and when Z is —N= then $R^{13}$ is absent;

m is 1, 2 or 3; and $R^6$ and $R^7$ are independently hydrogen, aminocarbonyl, alkoxycarbonyl optionally substituted alkyl or optionally substituted alkoxy, or $R^6$ and $R^7$ taken together with the carbon to which they are attached, form an optionally substituted 3- to 7-membered ring which optionally incorporates one or two additional heteroatoms, selected from N, O, and S in the ring;

provided that if $R^1$ is amino or if $R^1$ is heteroaryl or heterocycloalkyl with a heteroatom bonded to T, then T is not —O—, —S—, —O-alkyl, or —S-alkyl.

Also provided are pharmaceutical compositions comprising a pharmaceutically acceptable excipient and at least one chemical entity of as described herein.

Also provided are packaged pharmaceutical compositions, comprising a pharmaceutical composition as described herein and instructions for using the composition to treat a patient suffering from a heart disease.

Also provided are methods of treating heart disease in a mammal which method comprises administering to a mammal in need thereof a therapeutically effective amount of at least one chemical entity as described herein.

Also provided are methods for modulating the cardiac sarcomere in a mammal which method comprises administering to a mammal in need thereof a therapeutically effective amount of at least one chemical entity as described herein.

Also provided are methods for potentiating cardiac myosin in a mammal which method comprises administering to a mammal in need thereof a therapeutically effective amount of at least one chemical entity as described herein.

In certain embodiments, the present invention provides methods of screening for chemical entities that will bind to myosin (for example, myosin II or β myosin), for example chemical entities that will displace or compete with the binding of at least one chemical entity as described herein. The methods comprise combining an optionally-labeled compound of Formula I, myosin, and at least one candidate agent and determining the binding of the candidate agent to myosin.

In certain embodiments, the invention provides methods of screening for modulators of the activity of myosin. The methods comprise combining a compound of Formula I, myosin, and at least one candidate agent and determining the effect of the candidate agent on the activity of myosin.

Other embodiments will be apparent to those skilled in the art from the following detailed description.

As used in the present specification, the following words and phrases are generally intended to have the meanings as set forth below, except to the extent that the context in which they are used indicates otherwise. The following abbreviations and terms have the indicated meanings throughout:

Ac=acetyl
Boc=t-butyloxy carbonyl
c-=cyclo
CBZ=carbobenzoxy=benzyloxycarbonyl
DCM=dichloromethane=methylene chloride=$CH_2Cl_2$
DIEA=N,N-diisopropylethylamine
DMF=N,N-dimethylformamide
DMSO=dimethyl sulfoxide
Et=ethyl
EtOAc=ethyl acetate
EtOH=ethanol
GC=gas chromatograghy
h=hour
Me=methyl
min=minute
mL=milliliter
Ph=phenyl
PyBroP=bromo-tris-pyrrolidinophosphonium hexafluorophosphate
rt or RT=room temperature
s-=secondary
t- or tert-=tertiary
TFA=trifluoroacetic acid
THF=tetrahydrofuran
TLC=thin layer chromatography As used in the present specification, the following words and phrases are generally intended to have the meanings as set forth below, except to the extent that the context in which they are used indicates otherwise.

As used herein, when any variable occurs more than one time in a chemical formula, its definition on each occurrence is independent of its definition at every other occurrence.

A dash ("—") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric combinations having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to four carbons. "Lower alkylene" refers to alkylene groups having one to four carbons.

"Alkenyl" refers to an unsaturated branched or straight-chain alkyl group having at least one carbon-carbon double bond derived by the removal of one hydrogen atom from a single carbon atom of a parent alkene. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms.

"Alkynyl" refers to an unsaturated branched or straight-chain alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms.

"Cycloalkyl" indicates a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to four carbons.

"Mono- and di-alkylcarboxamide" encompasses a group of the formula —(C=O)NR$_a$R$_b$ where R$_a$ and R$_b$ are independently chosen from hydrogen and alkyl groups of the indicated number of carbon atoms, provided that R$_a$ and R$_b$ are not both hydrogen.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a C$_2$ acyl group is an acetyl group having the formula CH$_3$(C=O)—.

By "alkoxycarbonyl" is meant a group of the formula (alkoxy)(C=O)— attached through the carbonyl carbon wherein the alkoxy group has the indicated number of carbon atoms. Thus a C$_1$-C$_6$ alkoxycarbonyl group is an alkoxy group having from 1 to 6 carbon atoms attached through its oxygen to a carbonyl linker.

By "amino" is meant the group —NH$_2$.

"Mono- and di-(alkyl)amino" encompasses secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

The term "aminocarbonyl" refers to the group —CONR$^b$R$^c$, where
R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and
R$^c$ is independently chosen from hydrogen and optionally substituted C$_1$-C$_4$ alkyl; or
R$^b$ and R$^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;
where each substituted group is independently substituted with one or more substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

"Aryl" encompasses:
6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

"Carbamimidoyl" refers to the group —C(=NH)—NH$_2$.

"Substituted carbamimidoyl" refers to the group —C(=NR$^e$)—NR$^f$R$^g$ where R$^e$, is chosen from: hydrogen, cyano, optionally substituted alkyl, optionally substituted cycloalkyl, optionally substituted aryl, optionally substituted heteroaryl, and optionally substituted heterocycloalkyl; and R$^f$ and R$^g$ are independently chosen from: hydrogen optionally substituted alkyl, optionally substituted cycloalkyl, optionally substituted aryl, optionally substituted heteroaryl, and optionally substituted heterocycloalkyl, provided that at least one of R$^e$, R$^f$, and R$^g$ is not hydrogen and wherein substituted alkyl, cycloalkyl, aryl, heterocycloalkyl, and heteroaryl refer respectively to: alkyl, cycloalkyl, aryl, heterocycloalkyl, and heteroaryl wherein one or more (such as up to 5, for example, up to 3) hydrogen atoms are replaced by a substituent independently chosen from:
—R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substitutent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, sulfanyl (such as SR$^b$), sulfinyl (such as —SOR$^a$), and sulfonyl (such as —SO$_2$R$^a$ and —SO$_2$NR$^b$R$^c$),
where R$^a$ is chosen from optionally substituted C$_1$-C$_6$ alkyl, optionally substituted aryl, and optionally substituted heteroaryl;
R$^b$ is chosen from H, optionally substituted C$_1$-C$_6$ alkyl, optionally substituted aryl, and optionally substituted heteroaryl; and
R$^c$ is independently chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —CO$_2$H, —C(O)OC$_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, SO$_2$NH($C_1$-$C_4$ alkyl), —SO$_2$NH(phenyl), —NHSO$_2$($C_1$-$C_4$ alkyl), —NHSO2(phenyl), and —NHSO$_2$($C_1$-$C_4$ haloalkyl).

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses:
5- to 7-membered aromatic, monocyclic rings containing one or more, for example, from 1 to 4, or in certain embodiments, from 1 to 3, heteroatoms chosen from N, O, and S, with the remaining ring atoms being carbon;
bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and
tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—O$^-$) substituents, such as pyridinyl N-oxides.

By "heterocycloalkyl" is meant a single, non-aromatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "sulfanyl" includes the groups: —S-(optionally substituted ($C_1$-$C_6$)alkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

The term "sulfinyl" includes the groups: —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S(O$_2$)-(optionally substituted ($C_1$-$C_6$)alkyl), —S(O$_2$)-optionally substituted aryl), —S(O$_2$)-optionally substituted heteroaryl), —S(O$_2$)-(optionally substituted heterocycloalkyl), and —S(O$_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl;

$R^b$ is chosen from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for cycloalkyl, heterocycloalkyl, or heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)C(O)(C_1$-$C_4$ alkyl), —$N(C_1$-$C_4$ alkyl)C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for cycloalkyl, heterocycloalkyl, or heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)C(O)(C_1$-$C_4$ alkyl), —$N(C_1$-$C_4$ alkyl)C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

The term "substituted alkoxy" refers to alkoxy wherein the alkyl constituent is substituted (i.e., —O-(substituted alkyl)) wherein "substituted alkyl" refers to alkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is independently chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl). In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of 2-20, such as 2-10, and for example, 2-5. Another substituted alkoxy group is hydroxyalkoxy or —OCH$_2$(CH$_2$)$_y$OH, where y is an integer of 1-10, such as 1-4.

The term "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from:

—R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is independently chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

The term "substituted amino" refers to the group —NHR$^d$ or —NR$^d$R$^e$ wherein R$^d$ is chosen from: hydroxy, optionally substituted alkoxy, optionally substituted alkyl, optionally substituted cycloalkyl, optionally substituted acyl, optionally substituted carbamimidoyl, optionally substituted aminocarbonyl, optionally substituted aryl, optionally substituted heteroaryl, optionally substituted heterocycloalkyl, optionally substituted alkoxycarbonyl, optionally substituted sulfinyl and optionally substituted sulfonyl, and wherein R$^e$ is chosen from: optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is independently chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl); and wherein optionally substituted acyl, optionally substituted alkoxycarbonyl, sulfinyl and sulfonyl are as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds of Formula I include, but are not limited to, optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with carbon-carbon double bonds. Where compounds of Formula I exists in various tautomeric forms, chemical entities of the present invention include all tautomeric forms of the compound.

Chemical entities of the present invention include, but are not limited to compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I. The term "prodrugs" includes any chemical entities that become compounds of Formula I when administered to a patient, e.g., upon metabolic processing of the prodrug. Examples of prodrugs include, but are not limited to, acetate, formate, phosphate, and benzoate and like derivatives of functional groups (such as alcohol or amine groups) in the compounds of Formula I.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility. For example an active agent may be an anti-cancer therapeutic.

By "significant" is meant any detectable change that is statistically significant in a standard parametric test of statistical significance such as Student's T-test, where $p<0.05$.

The term "therapeutically effective amount" of a chemical entity of this invention means an amount effective, when administered to a human or non-human patient, to provide a therapeutic benefit such as amelioration of symptoms, slowing of disease progression, or prevention of disease.

"Treatment" or "treating" means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Patient" refers to an animal, such as a mammal, that has been or will be the object of treatment, observation or experiment. The methods of the invention can be useful in both human therapy and veterinary applications. In some embodiments, the patient is a mammal; in some embodiments the patient is human; and in some embodiments the patient is chosen from cats and dogs.

The present invention is directed to at least one chemical entity that is a selective modulator of the cardiac sarcomere (e.g., by stimulating or otherwise potentiating the activity of cardiac myosin).

Compounds can be named using the auto-naming feature in the ChemDraw Ultra 9.0 software package from CambridgeSoft. Compounds having the structure of Formula I can also be named and numbered (e.g., using ChemInnovation's Pipeline Pilot in connection with Chem 4-D Draw and the Nomenclator Module) as described below. For example, the compound of Formula II below

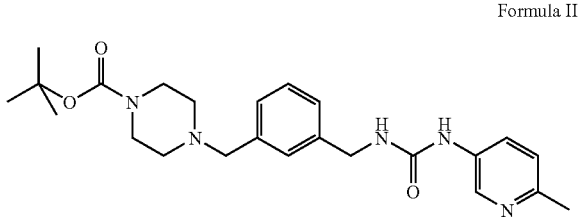

Formula II named tert-butyl 4-{[3-({[(6-methyl-3-pyridyl)amino]carbonylamino}methyl)phenyl]methyl}-piperazinecarboxylate, is a chemical entity of Formula I where $R^1$ is 4-(t-butoxycarbonyl)-piperidin-1-yl; $R^2$ is 6-methylpyridin-3-yl; m is 1; T is —$CH_2$—; and $R^3$, $R^4$, $R^5$, $R^6$, $R^7$, $R^{13}$, $R^{18}$ and $R^{19}$ are hydrogen.

The compound of Formula III below

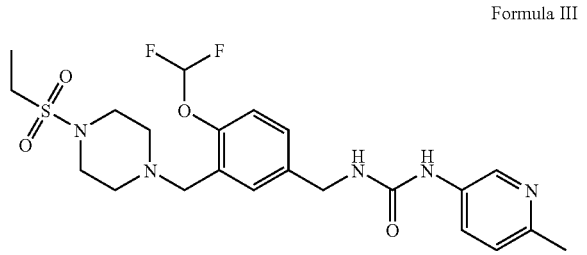

Formula III named N-[(4-(difluoromethoxy)-3-{[4-(ethylsulfonyl)piperazinyl]methyl}phenyl)methyl][(6-methyl(3-pyridyl))amino]carboxamide, is a chemical entity of Formula I where $R^1$ is 4-(ethylsulfonyl)-piperidin-1-yl; $R^2$ is 6-methylpyridin-3-yl; T is —$CH_2$—; $R^3$ is difluoromethoxy; m is 1; and $R^4$, $R^5$, $R^6$, $R^7$, $R^{13}$, $R^{18}$ and $R^{19}$ are hydrogen.

The present invention provides at least one chemical entity chosen from compounds of Formula I:

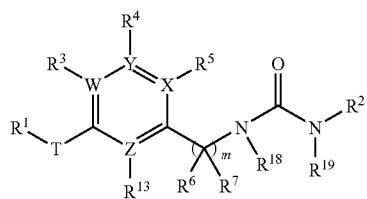

and pharmaceutically acceptable salts, solvates, chelates, non-covalent complexes, prodrugs, and mixtures thereof, wherein W, X, Y and Z are chosen from —CH= and —N=, provided that no more than two of W, X Y and Z are —N=;

T is selected from a bond, optionally substituted lower alkylene, —O—, —O-(optionally substituted lower alkylene)-, -(optionally substituted lower alkylene)-O—, —S—, —S-(optionally substituted lower alkylene)-, -(optionally substituted lower alkylene)-S—, —$SO_2$—, —$SO_2$-(optionally substituted lower alkylene)-, and -(optionally substituted lower alkylene)-$SO_2$—;

$R^{18}$ and $R^{19}$ are independently selected from hydrogen, optionally substituted alkyl, optionally substituted cycloalkyl, optionally substituted heteroalkyl, optionally substituted heterocycloalkyl, optionally substituted aryl and optionally substituted heteroaryl;

$R^1$ is chosen from optionally substituted alkyl, optionally substituted amino, optionally substituted aryl, optionally substituted heteroaryl, optionally substituted cycloalkyl and optionally substituted heterocycloalkyl;

$R^2$ is chosen from optionally substituted aryl, optionally substituted aralkyl; optionally substituted cycloalkyl, optionally substituted heteroaryl, optionally substituted heteroaralkyl and optionally substituted heterocycloalkyl;

$R^3$, $R^4$, $R^5$, and $R^{13}$ are independently chosen from hydrogen, halo, cyano, optionally substituted alkyl, optionally substituted alkoxy, optionally substituted heterocycloalkyl, and optionally substituted heteroaryl, provided that when W is —N= then $R^3$ is absent, when Y is —N= then $R^4$ is absent, when X is —N= then $R^5$ is absent, and when Z is —N= then $R^{13}$ is absent;

m is 1, 2 or 3; and $R^6$ and $R^7$ are independently hydrogen, aminocarbonyl, alkoxycarbonyl optionally substituted alkyl or optionally substituted alkoxy, or $R^6$ and $R^7$ taken together with the carbon to which they are attached, form an optionally substituted 3- to 7-membered ring which optionally incorporates one or two additional heteroatoms, selected from N, O, and S in the ring;

provided that if $R^1$ is amino or if $R^1$ is heteroaryl or heterocycloalkyl with a heteroatom bonded to T, then T is not —O—, —S—, —O-alkyl, or —S-alkyl.

In some embodiments, m is 1.
In some embodiments, m is 2.
In some embodiments, m is 3.
In some embodiments, T is chosen from a bond, optionally substituted alkylene, —O—, —O-(lower alkylene)-, -(lower alkylene)-O—, —S—, —S-(lower alkylene)-, and -(lower alkylene)-S—.
In some embodiments, T is a bond.
In some embodiments, T is —O—.
In some embodiments, T is lower alkyl substituted with optionally substituted with a group chosen from alkyl, optionally substituted alkoxy, and halo.
In some embodiments, T is chosen from —$CH_2$—, —$C(CH_3)H$—, —$C(CH_3)_2$—, —$CH_2CH_2$—, and —$CH_2CH_2CH_2$—.
In some embodiments, T is chosen from —$CH_2$—, —$C(CH_3)H$—, and —$C(CH_3)_2$—.
In some embodiments, T is —$CH_2$—.
In some embodiments, T is —$C(CH_3)H$—.
In some embodiments, T is —$C(CH_3)_2$—.
In some embodiments, $R^{18}$ and $R^{19}$ are independently selected from hydrogen, methyl and ethyl.
In some embodiments, each of $R^{18}$ and $R^{19}$ are independently selected from hydrogen and methyl.
In some embodiments, each of $R^{18}$ and $R^{19}$ are hydrogen.
In some embodiments, only one of W, X, Y and Z is —N=.
In some embodiments, two of W, X, Y and Z are —N=.
In some embodiments, $R^1$ is optionally substituted amino; optionally substituted piperazinyl; optionally substituted 1,1-dioxo-1$\lambda^6$-[1,2,5]thiadiazolidin-2-yl; optionally substituted 3-oxo-tetrahydro-pyrrolo[1,2-c]oxazol-6-yl, optionally substituted 2-oxo-imidazolidin-1-yl; optionally substituted morpholinyl; optionally substituted 1,1-dioxo-1$\lambda^6$-thiomorpholin-4-yl; optionally substituted pyrrolidinyl; optionally substituted piperidinyl; optionally substituted azepanyl; optionally substituted 1,4-diazepanyl; optionally substituted 3-oxo-tetrahydro-1H-oxazolo[3,4-a]pyrazin-3(5H)-one; optionally substituted 5,6,7,8-tetrahydro-[1,2,4]triazolo[4,3-a]pyrazinyl, and optionally substituted

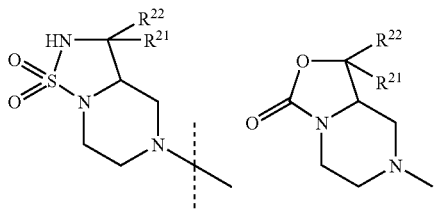

wherein $R^{21}$ and $R^{22}$ are independently chosen from hydrogen and optionally substituted alkyl, or $R^{21}$ and $R^{22}$ taken together with the carbon to which they are attached, form an optionally substituted 3- to 7-membered ring which optionally incorporates one or two additional heteroatoms, selected from N, O, and S in the ring.

In some embodiments, $R^1$ is selected from optionally substituted amino of the Formula $NR^{14}R^{10}$ where $R^{14}$ is selected from hydrogen, optionally substituted alkyl, optionally substituted acyl, optionally substituted alkoxycarbonyl, optionally substituted aminocarbonyl, and optionally substituted sulfonyl, and $R^{10}$ is selected from hydrogen and optionally substituted alkyl.

In some embodiments, $R^{14}$ is —$(SO_2)$—$R^{20}$ wherein $R^{20}$ is lower alkyl or —$NR^{11}R^{12}$ wherein $R^{11}$ and $R^{12}$ are independently hydrogen or lower alkyl.

In some embodiments, $R^{14}$ is optionally substituted lower alkoxycarbonyl.

In some embodiments, $R^{14}$ is lower alkyl.

In some embodiments, $R^{14}$ is acetyl.

In some embodiments, $R^{10}$ is selected from hydrogen, methyl, ethyl and methoxycarbonyl.

In some embodiments, $R^1$ is selected from amino, methylamino, 2-(methoxycarbonylamino), 2-(tert-butoxycarbonylamino), benzyloxycarbonylamino, ethylsulfonamido, N,N-dimethyl sulfamoylamino, acetylamino, 3,3-dimethylureido, methoxycarbonyl(methyl)amino, N,N-diethylamino, N-methylethylsulfonamido, N-acetyl-N-methylamino, N-t-butoxycarbonyl-N-methylamino, (N,N-dimethylsulfamoyl)(methyl)amino, 1,3,3-trimethylureido, bis(methoxycarbonyl)amino.

In some embodiments, each of $R^6$ and $R^7$ are independently selected from hydrogen, methyl and ethyl.

In some embodiments, each of $R^6$ and $R^7$ are independently selected from hydrogen and methyl.

In some embodiments, each of $R^6$ and $R^7$ are hydrogen.

In some embodiments, each of $R^6$ and $R^7$ are methyl.

In some embodiments, $R^6$ is methyl and $R^7$ is hydrogen.

In some embodiments, $R^2$ is selected from optionally substituted aryl, optionally substituted heteroaryl and optionally substituted heterocycloalkyl.

In some embodiments, $R^2$ is selected from optionally substituted phenyl, optionally substituted naphthyl, optionally substituted pyrrolyl, optionally substituted thiazolyl, optionally substituted isoxazolyl, optionally substituted pyrazolyl, optionally substituted oxazolyl, optionally substituted 1,3,4-oxadiazolyl, optionally substituted pyridinyl, optionally substituted pyrazinyl, optionally substituted pyrimidinyl and optionally substituted pyridazinyl.

In some embodiments, $R^2$ is chosen from optionally substituted pyridinyl, optionally substituted isoxazolyl and optionally substituted pyrimidinyl.

In some embodiments, $R^2$ is selected from 6-methylpyridin-3-yl, 6-acetylpyridin-3-yl, 6-cyanopyridin-3-yl, 6-methoxypyridin-3-yl, pyrimidin-5-yl, 2-methylpyrimidin-5-yl, and 3-methylisoxazol-5-yl.

In some embodiments, $R^2$ is selected from 6-methyl-pyridin-3-yl.

In some embodiments, each of $R^3$, $R^4$, $R^5$, and $R^{13}$ are independently chosen from hydrogen, halo optionally substituted alkyl and optionally substituted alkoxy.

In some embodiments, each of $R^3$, $R^4$, $R^5$, and $R^{13}$ are independently chosen from hydrogen, fluoro, chloro, methyl, trifluoromethoxy and difluoromethoxy.

In some embodiments, $R^3$ is chosen from methyl, chloro, fluoro and difluoromethoxy; and $R^4$, $R^5$, and $R^{13}$ are hydrogen.

In some embodiments, $R^4$ is chosen from methyl, chloro and fluoro; and $R^3$, $R^5$, and $R^{13}$ are hydrogen.

In some embodiments, $R^5$ is chosen from methyl, chloro, fluoro and difluoromethoxy; and $R^3$, $R^4$, and $R^{13}$ are hydrogen.

In some embodiments, $R^{13}$ is fluoro; and $R^4$, $R^5$, and $R^{13}$ are hydrogen.

In some embodiments, $R^5$ and $R^{13}$ are fluoro; and $R^3$ and $R^4$ are hydrogen.

In some embodiments, $R^3$ and $R^5$ are independently chosen from hydrogen, fluoro, chloro, difluoromethoxy and trifluoromethoxy; and $R^4$ and $R^{13}$ are hydrogen.

In some embodiments, each of $R^3$, $R^4$, $R^5$, and $R^{13}$ is hydrogen.

In some embodiments, the compounds of Formula I are chosen from compounds of Formula Ia

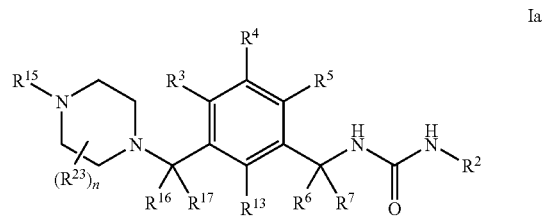

wherein $R^2$, $R^3$, $R^4$, $R^5$, $R^{13}$, $R^6$ and $R^7$ are as described herein;

$R^{15}$ is selected from hydrogen, cyano, optionally substituted acyl, optionally substituted alkoxycarbonyl, optionally substituted sulfonyl, optionally substituted aminocarbonyl, optionally substituted alkyl, optionally substituted aryl, optionally substituted cycloalkyl, optionally substituted heterocycloalkyl, and optionally substituted heteroaryl;

$R^{16}$ and $R^{17}$ are independently hydrogen, aminocarbonyl, alkoxycarbonyl, optionally substituted alkyl or optionally substituted alkoxy, or $R^{16}$ and $R^{17}$ taken together with the carbon to which they are attached, form an optionally substituted 3- to 7-membered ring which optionally incorporates one or two additional heteroatoms, selected from N, O, and S in the ring;

$R^{23}$ is selected from optionally substituted alkyl, optionally substituted alkoxy, optionally substituted acyl, optionally substituted alkoxycarbonyl, and optionally substituted aminocarbonyl; or when n is 2 or more, two $R^{23}$ can join together with any intervening atoms, to form an optionally substituted 3- to 7-membered ring which optionally incorporates one or two additional heteroatoms, selected from N, O, and S in the ring; and n is an integer from 0 to 4.

In some embodiments, n is 0.

In some embodiments, n is 1.

In some embodiments, wherein n is 2.

In some embodiments, n is 2 and both $R^{23}$ groups are bonded to the same carbon atom.

In some embodiments, $R^{23}$ is selected from methyl, methoxymethyl, carboxyl, methoxycarbonyl, ethoxycarbonyl, isopropoxycarbonyl, N-methylaminocarbonyl, N,N-dimethylaminocarbonyl, and azetidinylcarbonyl.

In some embodiments, n is 1 and $R^{23}$ is methyl.

In some embodiments, n is 2 and each $R^{23}$ is methyl.

In some embodiments, n is 2, each $R^{23}$ is methyl, and each $R^{23}$ is bonded to the same carbon atom.

In some embodiments, $R^{15}$ is selected from hydrogen, acetyl, cyano, methoxycarbonyl, ethoxycarbonyl, isopropoxycarbonyl, t-butoxycarbonyl, 2,2-dimethylpropanoyl, 2-methylpropanoyl, 3-methylbutanoyl, N,N-dimethylcarbamoyl, methylsulfonyl, ethylsulfonyl, propylsulfonyl, (dimethylamino)sulfonyl, and (isopropyl)sulfonyl.

In some embodiments, each of $R^{16}$ and $R^{17}$ are independently selected from hydrogen, methyl and ethyl.

In some embodiments, each of $R^{16}$ and $R^{17}$ are independently selected from hydrogen and methyl.

In some embodiments, each of $R^{16}$ and $R^{17}$ are hydrogen.

In some embodiments, each of $R^{16}$ and $R^{17}$ are methyl.

In some embodiments, $R^{16}$ is methyl and $R^{17}$ is hydrogen.

In some embodiments, $R^{16}$ and $R^{17}$ taken together with the carbon to which they are attached, form an optionally substituted 3- to 7-membered ring which optionally incorporates one or two additional heteroatoms, selected from N, O, and S in the ring.

In some embodiments, $R^{16}$ and $R^{17}$ taken together with the carbon to which they are attached, form a ring selected from optionally substituted cyclopropyl, optionally substituted cyclobutyl, optionally substituted cyclopentyl, optionally substituted cyclohexyl, optionally substituted cycloheptyl, optionally substituted furanyl, optionally substituted azetidinyl, optionally substituted pyrrolyl, optionally substituted thienyl, optionally substituted piperidinyl, optionally substituted piperazinyl, and optionally substituted tetrahydrofuranyl.

In some embodiments, the compound of Formula I is chosen from tert-butyl 4-{[3-({[(6-methyl-3-pyridyl)amino]carbonylamino}methyl)phenyl]methyl}-piperazinecarboxylate;

methyl 4-{[3-({[(6-methyl-3-pyridyl)amino]carbonylamino}methyl)phenyl]methyl}-piperazinecarboxylate;

N-[(3-{[4-(ethylsulfonyl)piperazinyl]methyl}phenyl)methyl][(6-methyl(3-pyridyl))amino]carboxamide;

N-({3-[(4-acetylpiperazinyl)methyl]phenyl}methyl)[(6-methyl(3-pyridyl))amino]carboxamide;

N-{[3-({4-[(dimethylamino)sulfonyl]piperazinyl}methyl)phenyl]methyl}[(6-methyl(3-pyridyl))amino]carboxamide;

tert-butyl 4-{[4-fluoro-3-({[(6-methyl(3-pyridyl))amino]carbonylamino}methyl)phenyl]-methyl}piperazinecarboxylate;

methyl 4-{[4-fluoro-3-({[(6-methyl(3-pyridyl))amino]carbonylamino}methyl)phenyl]-methyl}piperazinecarboxylate;

ethyl 4-{[4-fluoro-3-({[(6-methyl(3-pyridyl))amino]carbonylamino}methyl)phenyl]-methyl}piperazinecarboxylate;

N-({5-[(4-acetylpiperazinyl)methyl]-2-fluorophenyl}methyl)[(6-methyl(3-pyridyl))amino]carboxamide;

N-[(5-{[4-(N,N-dimethylcarbamoyl)piperazinyl]methyl}-2-fluorophenyl)methyl][(6-methyl(3-pyridyl))amino]carboxamide;

N-[(5-{[4-(ethylsulfonyl)piperazinyl]methyl}-2-fluorophenyl)methyl][(6-methyl(3-pyridyl))amino]carboxamide;

N-{[5-({4-[(dimethylamino)sulfonyl]piperazinyl}methyl)-2-fluorophenyl]methyl}[(6-methyl(3-pyridyl))amino]carboxamide;

methyl 4-{[2-fluoro-3-({[(6-methyl(3-pyridyl))amino]carbonylamino}methyl)phenyl]-methyl}piperazinecarboxylate;

N-[(3-{[4-(ethylsulfonyl)piperazinyl]methyl}-5-fluorophenyl)methyl][(6-methyl(3-pyridyl))amino]carboxamide;

methyl 4-{[2-chloro-5-({[(6-methyl(3-pyridyl))amino]carbonylamino}methyl)phenyl]-methyl}piperazinecarboxylate;

N-[(4-chloro-3-{[4-(ethylsulfonyl)piperazinyl]methyl}phenyl)methyl][(6-methyl(3-pyridyl))amino]carboxamide;

N-{[3-({4-[(dimethylamino)sulfonyl]piperazinyl}methyl)-4-chlorophenyl]methyl}[(6-methyl(3-pyridyl))amino]carboxamide;

N-[(3-{[4-(N,N-dimethylcarbamoyl)piperazinyl]methyl}-4-chlorophenyl)methyl][(6-methyl(3-pyridyl))amino]carboxamide;

N-({3-[(4-acetylpiperazinyl)methyl]-4-chlorophenyl}methyl)[(6-methyl(3-pyridyl))amino]carboxamide;

N-({4-chloro-3-[(4-cyanopiperazinyl)methyl]phenyl}methyl)[(6-methyl(3-pyridyl))amino]carboxamide;

N-{(1S)-1-[3-({4-[(dimethylamino)sulfonyl]piperazinyl}methyl)phenyl]ethyl}[(6-methyl(3-pyridyl))amino]carboxamide;

methyl 4-{[2-fluoro-5-({[(6-methyl(3-pyridyl))amino]carbonylamino}methyl)phenyl]-methyl}piperazinecarboxylate;

N-({3-[(4-acetylpiperazinyl)methyl]-4-fluorophenyl}methyl)[(6-methyl(3-pyridyl))amino]carboxamide;

N-[(3-{[4-(ethylsulfonyl)piperazinyl]methyl}-4-fluorophenyl)methyl][(6-methyl(3-pyridyl))amino]carboxamide;

N-[(3-{[4-(N,N-dimethylcarbamoyl)piperazinyl]methyl}-4-fluorophenyl)methyl][(6-methyl(3-pyridyl))amino]carboxamide;

N-{[3-({4-[(dimethylamino)sulfonyl]piperazinyl}methyl)-4-fluorophenyl]methyl}[(6-methyl(3-pyridyl))amino]carboxamide;

N-{[3-({4-[(dimethylamino)sulfonyl]piperazinyl}methyl)-5-chlorophenyl]methyl}[(6-methyl(3-pyridyl))amino]carboxamide;

N-({5-chloro-3-[(4-cyanopiperazinyl)methyl]phenyl}methyl)[(6-methyl(3-pyridyl))amino]carboxamide;

N-[(3-{[4-(ethylsulfonyl)piperazinyl]methyl}-5-methylphenyl)methyl][(6-methyl(3-pyridyl))amino]carboxamide;

N-({3-[(4-acetylpiperazinyl)methyl]-5-methylphenyl}methyl)[(6-methyl(3-pyridyl))amino]carboxamide;

N-{[3-({4-[(dimethylamino)sulfonyl]piperazinyl}methyl)-5-methylphenyl]methyl}[(6-methyl(3-pyridyl))amino]carboxamide;
N-[(3-{[4-(ethylsulfonyl)piperazinyl]methyl}-4-methylphenyl)methyl][(6-methyl(3-pyridyl))amino]carboxamide;
N-{[3-({4-[(dimethylamino)sulfonyl]piperazinyl}methyl)-4-methylphenyl]methyl}[(6-methyl(3-pyridyl))amino]carboxamide;
N-({3-[(4-acetylpiperazinyl)methyl]-4-methylphenyl}methyl)[(6-methyl(3-pyridyl))amino]carboxamide;
methyl 4-{[4-(difluoromethoxy)-3-({[(6-methyl(3-pyridyl))amino]carbonylamino}-methyl)phenyl]methyl}piperazinecarboxylate;
ethyl 4-{[4-(difluoromethoxy)-3-({[(6-methyl(3-pyridyl))amino]carbonylamino}-methyl)phenyl]methyl}piperazinecarboxylate;
ethyl 4-{[3-({[(6-cyano-3-pyridyl))amino]carbonylamino}methyl)-4-fluorophenyl]methyl}piperazinecarboxylate;
methyl 4-{[2-methyl-5-({[(6-methyl(3-pyridyl))amino]carbonylamino}methyl)phenyl]-methyl}piperazinecarboxylate;
ethyl 4-{[4-fluoro-3-({[(6-methoxy(3-pyridyl))amino]carbonylamino}methyl)phenyl]-methyl}piperazinecarboxylate;
ethyl 4-[(4-fluoro-3-{[(pyrimidin-5-ylamino)carbonylamino]methyl}phenyl)methyl]-piperazinecarboxylate;
N-[(2-fluoro-5-{[4-(methylsulfonyl)piperazinyl]methyl}phenyl)methyl][(6-methyl(3-pyridyl))amino]carboxamide;
methylethyl 4-{[4-fluoro-3-({[(6-methyl(3-pyridyl))amino]carbonylamino}methyl)-phenyl]methyl}piperazinecarboxylate;
N-{[2-fluoro-5-({4-[(methylethyl)sulfonyl]piperazinyl}methyl)phenyl]methyl}[(6-methyl(3-pyridyl))amino]carboxamide;
N-[(2-fluoro-5-{[4-(3-methylbutanoyl)piperazinyl]methyl}phenyl)methyl][(6-methyl(3-pyridyl))amino]carboxamide;
N-[(2-fluoro-5-{[4-(propylsulfonyl)piperazinyl]methyl}phenyl)methyl][(6-methyl(3-pyridyl))amino]carboxamide;
N-[(5-{[4-(2,2-dimethylpropanoyl)piperazinyl]methyl}-2-fluorophenyl)methyl][(6-methyl(3-pyridyl))amino]carboxamide.
ethyl 4-{[2-(difluoromethoxy)-5-({[(6-methyl(3-pyridyl))amino]carbonylamino}-methyl)phenyl]methyl}piperazinecarboxylate;
N-[(4-(difluoromethoxy)-3-{[4-(ethylsulfonyl)piperazinyl]methyl}phenyl)methyl][(6-methyl(3-pyridyl))amino]carboxamide;
N-[(4-(difluoromethoxy)-3-{[4-(methylsulfonyl)piperazinyl]methyl}phenyl)methyl][(6-methyl(3-pyridyl))amino]carboxamide;
ethyl 4-{[4-fluoro-3-({[(3-methylisoxazol-5-yl)amino]carbonylamino}methyl)phenyl]-methyl}piperazinecarboxylate;
ethyl 4-{[3-({[(6-acetyl(3-pyridyl))amino]carbonylamino}methyl)-4-fluorophenyl]methyl}piperazinecarboxylate;
methyl 4-{[4-methyl-3-({[(6-methyl(3-pyridyl))amino]carbonylamino}methyl)phenyl]-methyl}piperazinecarboxylate;
ethyl 4-{[4-methyl-3-({[(6-methyl(3-pyridyl))amino]carbonylamino}methyl)phenyl]-methyl}piperazinecarboxylate;
methylethyl 4-{[4-methyl-3-({[(6-methyl(3-pyridyl))amino]carbonylamino}methyl)-phenyl]methyl}piperazinecarboxylate;
N-[(5-{[4-(ethylsulfonyl)piperazinyl]methyl}-2-methylphenyl)methyl][(6-methyl(3-pyridyl))amino]carboxamide;
N-({5-[(4-acetylpiperazinyl)methyl]-2-methylphenyl}methyl)[(6-methyl(3-pyridyl))amino]carboxamide;
[(6-methyl(3-pyridyl))amino]-N-[(2-methyl-5-{[4-(methylsulfonyl)piperazinyl]-methyl}phenyl)methyl]carboxamide;
[(6-methyl(3-pyridyl))amino]-N-{[2-methyl-5-({4-[(methylethyl)sulfonyl]piperazinyl}-methyl)phenyl]methyl}carboxamide;
[(6-methyl(3-pyridyl))amino]-N-[(2-methyl-5-{[4-(2-methylpropanoyl)piperazinyl]-methyl}phenyl)methyl]carboxamide;
tert-butyl 4-{[2,4-difluoro-3-({[(6-methyl(3-pyridyl))amino]carbonylamino}-methyl)phenyl]methyl}piperazinecarboxylate;
methyl 4-{[2,4-difluoro-3-({[(6-methyl(3-pyridyl))amino]carbonylamino}-methyl)phenyl]methyl}piperazinecarboxylate;
ethyl 4-{[2,4-difluoro-3-({[(6-methyl(3-pyridyl))amino]carbonylamino}-methyl)phenyl]methyl}piperazinecarboxylate;
N-({3-[(4-acetylpiperazinyl)methyl]-2,6-difluorophenyl}methyl)[(6-methyl(3-pyridyl))amino]carboxamide;
N-[(2,6-difluoro-3-{[4-(methylsulfonyl)piperazinyl]methyl}phenyl)methyl][(6-methyl(3-pyridyl))amino]carboxamide;
N-[(3-{[4-(ethylsulfonyl)piperazinyl]methyl}-2,6-difluorophenyl)methyl][(6-methyl(3-pyridyl))amino]carboxamide;
N-{[3-({4-[(dimethylamino)sulfonyl]piperazinyl}methyl)-2,6-difluorophenyl]methyl}[(6-methyl(3-pyridyl))amino]carboxamide;
[(6-cyano(3-pyridyl))amino]-N-[(5-{[4-(ethylsulfonyl)piperazinyl]methyl}-2-fluorophenyl)methyl]carboxamide;
[(6-acetyl(3-pyridyl))amino]-N-[(5-{[4-(ethylsulfonyl)piperazinyl]methyl}-2-fluorophenyl)methyl]carboxamide;
ethyl 4-{[4-fluoro-3-({[(2-methylpyrimidin-5-yl)amino]carbonylamino}methyl)phenyl]-methyl}piperazinecarboxylate;
N-[(5-{[4-(ethylsulfonyl)piperazinyl]methyl}-2-fluorophenyl)methyl][(6-methoxy(3-pyridyl))amino]carboxamide;
N-[(5-{[4-(ethylsulfonyl)piperazinyl]methyl}-2-fluorophenyl)methyl](pyrimidin-5-ylamino)carboxamide;
tert-butyl 4-{[4-chloro-3-({[(6-methyl(3-pyridyl))amino]carbonylamino}methyl)phenyl]-methyl}piperazinecarboxylate;
N-[(5-{[4-(ethylsulfonyl)piperazinyl]methyl}-2-fluorophenyl)methyl][(2-methylpyrimidin-5-yl)amino]carboxamide;
N-{[2-chloro-5-(piperazinylmethyl)phenyl]methyl}[(6-methyl(3-pyridyl))amino]carboxamide;
methyl 4-{[4-chloro-3-({[(6-methyl(3-pyridyl))amino]carbonylamino}methyl)-phenyl]methyl}piperazinecarboxylate;
N-[(2-chloro-5-{[4-(methylsulfonyl)piperazinyl]methyl}phenyl)methyl][(6-methyl(3-pyridyl))amino]carboxamide;
N-[(2-chloro-5-{[4-(ethylsulfonyl)piperazinyl]methyl}phenyl)methyl][(6-methyl(3-pyridyl))amino]carboxamide;

N-{[3-((3R)-1-acetyl(3-piperidyloxy))-5-fluorophenyl]methyl}[(6-methoxy(3-pyridyl))amino]carboxamide;

N-{[3-((3R)-1-acetyl(3-piperidyloxy))-5-fluorophenyl]methyl}[(6-methyl(3-pyridyl))amino]carboxamide;

N-{[3-((3R)-1-acetyl(3-piperidyloxy))-5-fluorophenyl]methyl}[(6-ethynyl(3-pyridyl))amino]carboxamide;

{(3R)-3-[5-fluoro-3-({[(6-methyl(3-pyridyl))amino]carbonylamino}methyl)phenoxy]piperidyl}-N,N-dimethylcarboxamide;

N-({3-[(3R)-1-(methylsulfonyl)(3-piperidyloxy)]-5-fluorophenyl}methyl)[(6-methyl(3-pyridyl))amino]carboxamide;

N-{[3-((3R)-1-formyl(3-piperidyloxy))-5-fluorophenyl]methyl}[(6-methyl(3-pyridyl))amino]carboxamide;

methyl (3R)-3-[5-fluoro-3-({[(6-methyl(3-pyridyl))amino]carbonylamino}methyl)phenoxy]piperidinecarboxylate;

N-{2-[3-((3R)-1-acetyl(3-piperidyloxy))-5-fluorophenyl]ethyl}[(6-methyl(3-pyridyl))amino]carboxamide;

N-{[3-((3R)-1-acetyl(3-piperidyloxy))-5-fluorophenyl]methyl}[(6-ethyl(3-pyridyl))amino]carboxamide;

N-{2-[3-((3R)-1-acetyl(3-piperidyloxy))-5-fluorophenyl]ethyl}(3-pyridylamino)carboxamide;

tert-butyl (3R)-3-(5-fluoro-3-{2-[(3-pyridylamino)carbonylamino]ethyl}phenoxy)piperidinecarboxylate;

N-{2-[3-((3R)-1-acetyl(3-piperidyloxy))-5-fluorophenyl]ethyl}[(6-ethyl(3-pyridyl))amino]carboxamide;

N-{[3-((3R)-1-acetyl(3-piperidyloxy))-5-fluorophenyl]ethyl}(3-pyridylamino)carboxamide;

N-{[3-((3R)-1-acetyl(3-piperidyloxy))-5-fluorophenyl]ethyl}[(6-methyl(3-pyridyl))amino]carboxamide, tert-butyl 4-{2-[3-({[(6-methyl-3-pyridyl)amino]carbonylamino}methyl)phenyl]ethyl}piperazinecarboxylate;

tert-butyl 4-{[2-({[(6-methyl-3-pyridyl)amino]carbonylamino}methyl)-4-pyridyl]methyl}piperazinecarboxylate;

N-{[3-(2-{4-[(dimethylamino)sulfonyl]piperazinyl}ethyl)phenyl]methyl}[(6-methyl(3-pyridyl))amino]carboxamide;

N-{[4-({4-[(dimethylamino)sulfonyl]piperazinyl}methyl)(2-pyridyl)]methyl}[(6-methyl(3-pyridyl))amino]carboxamide;

N-{[4-({4-[(dimethylamino)sulfonyl]piperazinyl}methyl)phenyl]methyl}[(6-methyl(3-pyridyl))amino]carboxamide;

N-[4-({4-[(dimethylamino)sulfonyl]piperazinyl}methyl)-3-fluoro(2-pyridyl)][(6-methyl(3-pyridyl))amino]carboxamide;

N-[(5-{[4-(ethylsulfonyl)piperazinyl]methyl}-2-fluorophenyl)methyl][(6-methoxy(3-pyridyl))amino]carboxamide;

N-[(5-{[4-(ethylsulfonyl)piperazinyl]methyl}-2-fluorophenyl)methyl][(6-methyl(3-pyridyl))amino]carboxamide;

N-[(4-{[4-(ethylsulfonyl)piperazinyl]methyl}(2-pyridyl))methyl][(6-methyl(3-pyridyl))amino]carboxamide;

N-[(3-{2-[4-(ethylsulfonyl)piperazinyl]ethyl}phenyl)methyl][(6-methyl(3-pyridyl))amino]carboxamide;

N-[(3-fluoro-6-{[4-(methylsulfonyl)piperazinyl]methyl}(2-pyridyl))methyl][(6-methyl(3-pyridyl))amino]carboxamide;

N-({3-[2-(4-acetylpiperazinyl)ethyl]phenyl}methyl)[(6-methyl(3-pyridyl))amino]carboxamide;

N-({4-[(4-acetylpiperazinyl)methyl](2-pyridyl)}methyl)[(6-methyl(3-pyridyl))amino]carboxamide; and methyl 4-{2-[3-({[(6-methyl-3-pyridyl)amino]carbonylamino}methyl)phenyl]ethyl}piperazinecarboxylate, and pharmaceutically acceptable salts, solvates, chelates, non-covalent complexes, prodrugs, and mixtures thereof.

Chemical entities of the invention can be synthesized utilizing techniques well known in the art, e.g., as illustrated below with reference to the Reaction Schemes.

Unless specified to the contrary, the reactions described herein take place at atmospheric pressure, generally within a temperature range from −10° C. to 110° C. Further, except as employed in the Examples or as otherwise specified, reaction times and conditions are intended to be approximate, e.g., taking place at about atmospheric pressure within a temperature range of about −10° Cl to about 110° C. over a period of about 1 to about 24 hours; reactions left to run overnight average a period of about 16 hours.

The terms "solvent", "organic solvent" or "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can, of course, also be used.

When desired, the (R)— and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. For example, a compound of Formula I can be dissolved in a lower alkanol and placed on a Chiralpak AD (205×20 mm) column (Chiral Technologies, Inc.) conditioned for 60 min at 70% EtOAc in Hexane. It will be appreciated that where the desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts or solvents, or by converting one enantiomer to the other by asymmetric transformation.

It will be appreciated by those skilled in the art that one or more of the reactants, steps and/or conditions described in the reaction schemes may require adjustment to accommodate various substituents at $R_1$ and $R_2$.

Many of the optionally substituted starting compounds 101, 103, 201, 301 and other reactants are commercially available, e.g., from Aldrich Chemical Company (Milwaukee, Wis.) or can be readily prepared by those skilled in the art using commonly employed synthetic methodology.

REACTION SCHEME 1

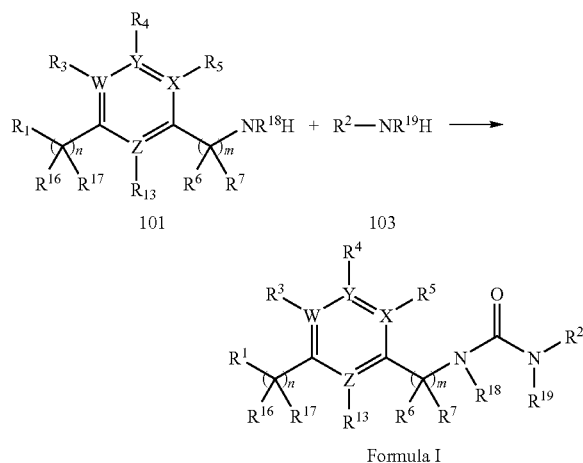

Preparation of Compounds of Formula I Referring to Reaction Scheme 1, a flask equipped with a magnetic stirrer, reflux condenser and thermal well, under nitrogen, is charged with phosgene or a phosgene equivalent (typically triphosgene) and a nonpolar, aprotic solvent such as dichloromethane or tetrahydrofuran. A solution of a compound of Formula 101 in a nonpolar, aprotic solvent such as dichloromethane or tetrahydrofuran is added dropwise over about 10-60 minutes and the solution is allowed to stir between 1 to 15 hr. A compound of Formula 103 is added portionwise, and the solution is stirred for about 10-60 min. A base, such as DIEA, is added dropwise for about one hour, and the solution is allowed to stir for about 1-15 hr. The product, a compound of Formula I, is isolated and purified.

REACTION SCHEME 2

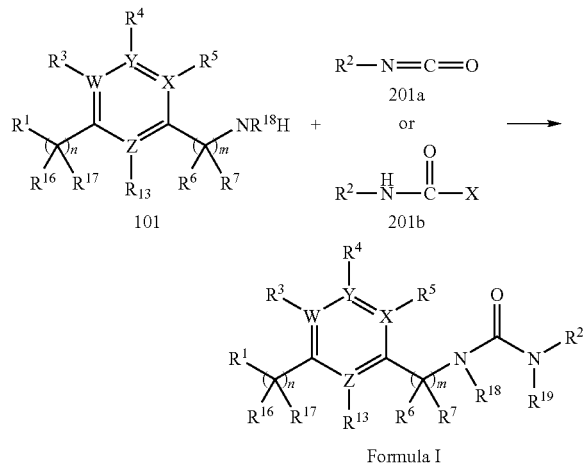

Preparation of Compounds of Formula I Reaction Scheme 2 illustrates an alternative synthesis of compounds of Formula I. The isocyanate of Formula 201a can be formed and isolated independently from either corresponding amine (i.e., $R^2$—NH2) using phosgene or a phosgene equivalent or from the corresponding carboxylic acid (i.e., $R^2$—COOH) using a Curtius or Hoffman rearrangement. Alternatively, the compound in Formula 201b wherein X is equal to a leaving group such as p-nitrophenol can be made in situ (e.g., Izdebski, J.; Pawlak, D. Synthesis (1989) 423-425.). A mixture of compounds of Formula 101 and 201 in an aprotic solvent such as dichloromethane or tetrahydrofuran from –40° C. to 110° C. is allowed to stir for between 1 to 15 hr. The product, a compound of Formula I, is isolated and purified.

Preparation of Compounds of Formula II Referring to Reaction Scheme 3, below, the benzylic alcohol of Formula 301 is converted to a leaving group ("Lv" such as halo, mesylate or triflate), 302 using commonly employed synthetic methodology (for example. see: "Comprehensive Organic Transformations" Larock, Richard C., 1989, VCH publishers, Inc. p. 353-365, which is incorporated herein by reference).

A mixture of a compound of Formula 302 and amine of formula $HNR_8R_9$ in an aprotic solvent such as dichloromethane or DMF from –40° C. to 110° C. is allowed to stir for between 1 to 15 hr. The product, a compound of Formula II, is isolated and purified.

Alternatively, the benzylic alcohol of Formula 301 is oxidized to the aldehyde of Formula 303 using commonly employed synthetic methodology (for example see: "Comprehensive Organic Transformations" Larock, Richard C., 1989, VCH publishers, Inc. p. 604-615, which is incorporated herein by reference.).

REACTION SCHEME 3

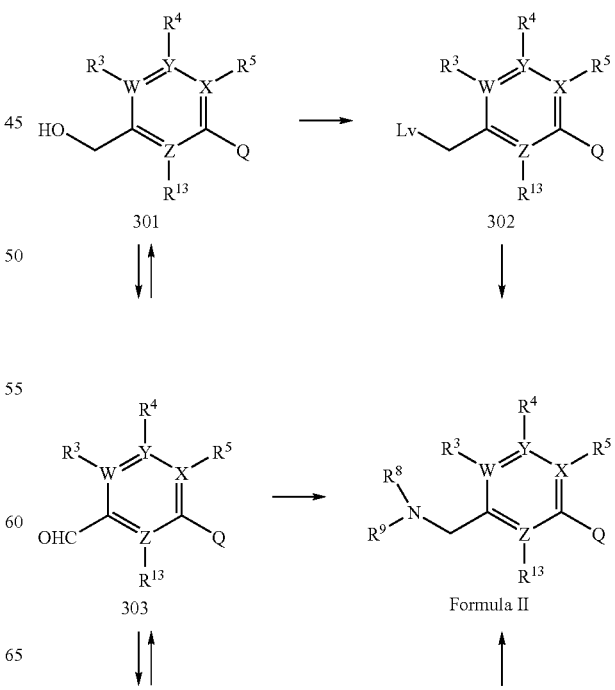

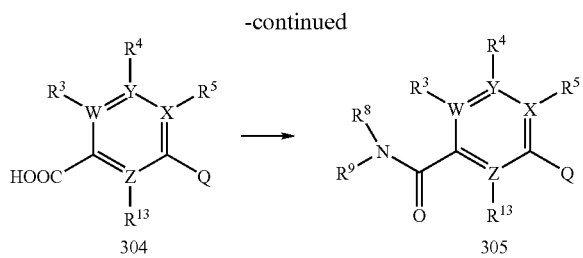

304 → 305

A mixture of a compound of Formula 303 and amine of formula HNR⁸R⁹ in a solvent such as dichloromethane with a reducing agent such as triacetoxyborohydride with or without an acid such as acetic acid from −40° C. to 110° C. is allowed to stir for between 1 to 36 hr. The product, a compound of Formula II, is isolated and purified.

Alternatively, the carboxylic acid of Formula 304 is coupled to an amine to using commonly employed synthetic methodology (for example see: "Comprehensive Organic Transformations" Larock, Richard C., 1989, VCH publishers, Inc. p. 972-976, which is incorporated herein by reference) to form amide 305. Amide 305 is reduced to a compound of Formula II using commonly employed synthetic methodology such as treating 305 with borane-dimethylsulfide in THF from −40° C. to reflux for 1 to 96 hr.

A compound of Formula II wherein Q is cyano, —CR⁶R⁷-bromo, —CR⁶R⁷-chloro, —CR⁶R⁷-nitro, —CR⁶R⁷-cyano, —CR⁶R⁷-amino, or a protected —CR⁶R⁷-amino can be conferred to a compound of Formula 101 using commonly employed synthetic methodology. For example, when Q is cyano, it may be reduced to the corresponding amine using BH₃ or hydrogen with a Pd/C catalyst with or without an acid such as hydrochloric acid.

Preparation of Specific Enantiomers of Formula I As discussed above, a specific enantiomer of Formula I can be synthesized by asymmetric synthesis using optically active reagents, substrates, catalysts or solvents, or by converting one enantiomer to the other by asymmetric transformation. For example, (R)— and (S)-3-hydroxypiperidine are commercially available are commercially available from Sigma-Aldrich, as are (R)— and (S)-hydroxypyrrolidine; they can also be resolved [e.g., using (6,6-dimethyl-2-oxo-adamantan-1-yl)-methane sulfonic acid, see: Ringdahl et. al, *J. Chem. Soc. Perkin Trans. II*, 1981, 4, 697-8] and via other published methodology.

While it is well known that pharmaceuticals must meet pharmacopoeia standards before approval and/or marketing, and that synthetic reagents (such as the various substituted amines or alcohols) and precursors should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a synthetic process of the invention.

A racemic mixture of isomers of a compound of Formula I is optionally placed on a chiral chromatography column and separated into (R)— and (S)-enantiomers.

A compound of Formula I is optionally contacted with a pharmaceutically acceptable acid to form the corresponding acid addition salt.

A pharmaceutically acceptable acid addition salt of Formula I is optionally contacted with a base to form the corresponding free base of Formula I.

The chemical entities of the present invention are selective for and modulate the cardiac sarcomere, and are useful to bind to and/or potentiate the activity of cardiac myosin, increasing the rate at which myosin hydrolyzes ATP. As used in this context, "modulate" means either increasing or decreasing myosin activity, whereas "potentiate" means to increase activity. It has also been determined in testing representative chemical entities of the invention, that their administration can also increase the contractile force in cardiac muscle fiber.

The chemical entities, pharmaceutical formulations and methods of the invention are used to treat heart disease, including but not limited to: acute (or decompensated) congestive heart failure, and chronic congestive heart failure; for example, diseases associated with systolic heart dysfunction. Additional therapeutic utilities include administration to stabilize heart function in patients awaiting a heart transplant, and to assist a stopped or slowed heart in resuming normal function following use of a bypass pump.

ATP hydrolysis is employed by myosin in the sarcomere to produce force. Therefore, an increase in ATP hydrolysis would correspond to an increase in the force or velocity of muscle contraction. In the presence of actin, myosin ATPase activity is stimulated >100 fold. Thus, ATP hydrolysis not only measures myosin enzymatic activity but also its interaction with the actin filament. A chemical entity that modulates the cardiac sarcomere can be identified by an increase or decrease in the rate of ATP hydrolysis by myosin, for example exhibiting a 1.4 fold increase at concentrations less than 10 μM (for example, less than 1 μM). Some assays for such activity will employ myosin from a human source, although myosin from other organisms can also be used. Systems that model the regulatory role of calcium in myosin binding are also useful.

Alternatively, a biochemically functional sarcomere preparation can be used to determine in vitro ATPase activity, for example, as described in U.S. Ser. No. 09/539,164, filed Mar. 29, 2000. The functional biochemical behavior of the sarcomere, including calcium sensitivity of ATPase hydrolysis, can be reconstituted by combining its purified individual components (including its regulatory components and myosin). Another functional preparation is the in vitro motility assay. It can be performed by adding test chemical entity to a myosin-bound slide and observing the velocity of actin filaments sliding over the myosin covered glass surface (Kron S J. (1991) Methods Enzymol. 196:399-416).

The in vitro rate of ATP hydrolysis correlates to myosin potentiating activity, which can be determined by monitoring the production of either ADP or phosphate, for example as described in Ser. No. 09/314,464, filed May 18, 1999. ADP production can also be monitored by coupling the ADP production to NADH oxidation (using the enzymes pyruvate kinase and lactate dehydrogenase) and monitoring the NADH level either by absorbance or fluorescence (Greengard, P., *Nature* 178 (Part 4534): 632-634 (1956); *Mol Pharmacol* January 1970; 6(1):31-40). Phosphate production can be monitored using purine nucleoside phosphorylase to couple phosphate production to the cleavage of a purine analog, which results in either a change in absorbance (*Proc Natl Acad Sci USA* Jun. 1, 1992; 89(11):4884-7) or fluorescence (*Biochem J* Mar. 1, 1990; 266(2):611-4). While a single measurement can be employed, multiple measurements may be taken of the same sample at different times in order to determine the absolute rate of the protein activity; such measurements can have higher specificity in the presence of test chemical entities that have similar absorbance or fluorescence properties with those of the enzymatic readout.

Test chemical entities can be assayed in a highly parallel fashion using multiwell plates by placing the chemical entities either individually in wells or testing them in mixtures. Assay components including the target protein complex, coupling enzymes and substrates, and ATP can then be added to the wells and the absorbance or fluorescence of each well of the plate can be measured with a plate reader.

One method uses a 384 well plate format and a 25 µL reaction volume. A pyruvate kinase/lactate dehydrogenase coupled enzyme system (Huang T G and Hackney D D. (1994) J Biol Chem 269(23): 16493-16501) is used to measure the rate of ATP hydrolysis in each well. As will be appreciated by those in the art, the assay components are added in buffers and reagents. Since the methods outlined herein allow kinetic measurements, incubation periods are optimized to give adequate detection signals over the background. The assay is done in real time giving the kinetics of ATP hydrolysis, which increases the signal to noise ratio of the assay.

Modulation of cardiac muscle fiber contractile force can be measured using detergent permeabilized cardiac fibers (also referred to as skinned cardiac fibers), for example, as described by Haikala H, et al (1995) J Cardiovasc Pharmacol 25(5):794-801. Skinned cardiac fibers retain their intrinsic sarcomeric organization, but do not retain all aspects of cellular calcium cycling. This model offers two advantages: first, the cellular membrane is not a barrier to chemical entity penetration, and second, calcium concentration is controlled. Therefore, any increase in contractile force is a direct measure of the test chemical entity's effect on sarcomeric proteins. Tension measurements are made by mounting one end of the muscle fiber to a stationary post and the other end to a transducer that can measure force. After stretching the fiber to remove slack, the force transducer records increased tension as the fiber begins to contract. This measurement is called the isometric tension, since the fiber is not allowed to shorten. Activation of the permeabilized muscle fiber is accomplished by placing it in a buffered calcium solution, followed by addition of test chemical entity or control. When tested in this manner, chemical entities of the invention caused an increase in force at calcium concentrations associated with physiologic contractile activity, but very little augmentation of force in relaxing buffer at low calcium concentrations or in the absence of calcium (the EGTA data point).

Selectivity for the cardiac sarcomere and cardiac myosin can be determined by substituting non-cardiac sarcomere components and myosin in one or more of the above-described assays and comparing the results obtained against those obtained using the cardiac equivalents.

A chemical entity's ability to increase observed ATPase rate in an in vitro reconstituted sarcomere assay could result from the increased turnover rate of S1-myosin or, alternatively, increased sensitivity of a decorated actin filament to $Ca^{++}$-activation. To distinguish between these two possible modes of action, the effect of the chemical entity on ATPase activity of S1 with undecorated actin filaments is initially measured. If an increase of activity is observed, the chemical entity's effect on the Ca-responsive regulatory apparatus could be disproved. A second, more sensitive assay can be employed to identify chemical entities whose activating effect on S1-myosin is enhanced in the presence of a decorated actin (compared to pure actin filaments). In this second assay activities of cardiac-S1 and skeletal-S1 on cardiac and skeletal regulated actin filaments (in all 4 permutations) are compared. A chemical entity that displays its effect on cardiac-S1/cardiac actin and cardiac-S1/skeletal actin, but not on skeletal-S1/skeletal actin and skeletal-S1/cardiac actin systems, can be confidently classified as cardiac-S1 activator.

Initial evaluation of in vivo activity can be determined in cellular models of myocyte contractility, e.g., as described by Popping S, et al ((1996) Am. J. Physiol. 271: H357-H364) and Wolska B M, et al ((1996) Am. J. Physiol. 39:H24-H32). One advantage of the myocyte model is that the component systems that result in changes in contractility can be isolated and the major site(s) of action determined. Chemical entities with cellular activity (for example, selecting chemical entities having the following profile: >120% increase in fractional shortening over basal at 2 µM, limited changes in diastolic length (<5% change), and no significant decrease in contraction or relaxation velocities) can then be assessed in whole organ models, such as such as the Isolated Heart (Langendorff) model of cardiac function, in vivo using echocardiography or invasive hemodynamic measures, and in animal-based heart failure models, such as the Rat Left Coronary Artery Occlusion model. Ultimately, activity for treating heart disease is demonstrated in blinded, placebo-controlled, human clinical trials.

At least one chemical entity as described herein is administered at a therapeutically effective dosage, e.g., a dosage sufficient to provide treatment for the disease states previously described. While human dosage levels have yet to be optimized for the chemical entities of the invention, generally, a daily dose is from about 0.05 to 100 mg/kg of body weight, for example about 0.10 to 10.0 mg/kg of body weight, or, for example, about 0.15 to 1.0 mg/kg of body weight. Thus, for administration to a 70 kg person, the dosage range would be about 3.5 to 7000 mg per day, for example, about 7.0 to 700.0 mg per day, or for example, about 10.0 to 100.0 mg per day. The amount of active chemical entity administered will, of course, be dependent on the subject and disease state being treated, the severity of the affliction, the manner and schedule of administration and the judgment of the prescribing physician; for example, a likely dose range for oral administration would be about 70 to 700 mg per day, whereas for intravenous administration a likely dose range would be about 700 to 7000 mg per day, the active agents being selected for longer or shorter plasma half-lives, respectively.

Administration of the chemical entities of the invention can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administration are customary in treating the indications that are the subject of the present invention.

Pharmaceutically acceptable compositions include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrin derivatives, sorbitan monolaurate, triethanolamine acetate, triethanolamine oleate, and the like). Generally, depending on the intended mode of administration, the pharmaceutical formulation will contain about 0.005% to 95%, or about 0.5% to 50% by weight of a chemical entity of the invention. Actual methods of preparing such dosage forms are known, or will be apparent, to those skilled in this art; for example, see *Remington's Pharmaceutical Sciences*, Mack Publishing Company, Easton, Penn.

In addition, the chemical entities of the invention can be co-administered with, and the pharmaceutical compositions can include, other medicinal agents, pharmaceutical agents, adjuvants, and the like. Suitable additional active agents include, for example: therapies that retard the progression of heart failure by down-regulating neurohormonal stimulation of the heart and attempt to prevent cardiac remodeling (e.g., ACE inhibitors or β-blockers); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide).

In one embodiment, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. an active chemical entity as defined above and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of active chemical entity contained in such parenteral compositions is highly dependent on the specific nature thereof, as well as the activity of the chemical entity and the needs of the subject. However, percentages of active ingredient of 0.01% to 10% in solution are employable, and will be higher if the composition is a solid that will be subsequently diluted to the above percentages. In certain embodiments, the composition will comprise 0.2-2% of the active agent in solution.

Formulations of the active chemical entity may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example, less than 10 microns.

Generally, to employ the chemical entities of the invention in a method of screening for myosin binding, myosin is bound to a support and a chemical entity of the invention is added to the assay. Alternatively, the chemical entity of the invention can be bound to the support and the myosin added. Classes of compounds among which novel binding agents may be sought include specific antibodies, non-natural binding agents identified in screens of chemical libraries, peptide analogs, etc. Of interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like. See, e.g., U.S. Pat. No. 6,495,337, incorporated herein by reference.

The following examples serve to more fully describe the manner of using the above-described invention. It is understood that these examples in no way serve to limit the true scope of this invention, but rather are presented for illustrative purposes. All references cited herein are incorporated by reference in their entirety.

EXAMPLES

Example 1

1-(2-Chloro-5-((4-(methylsulfonyl)piperazin-1-yl)methyl)benzyl)-3-(6-methylpyridin-3-yl)urea tert-butyl 4-(4-chloro-3-cyanobenzoyl)piperazine-1-carboxylate. In a 100 mL round-bottom flask under a positive nitrogen pressure of 4-chloro-3-cyanobenzoic acid (4.28 mmol), 1-(tert-butoxycarbonyl)piperazine (1.59 g, 8.56.mmol), EDC (903 mg, 4.71 mmol) and HOBT (694 mg, 5.14 mmol) were dissolved in 17 mL of $CH_2Cl_2$. Triethylamine (1.5 mL, 10.7 mmol) was added and the reaction mixture was stirred for 20 h. After this time additional quantities of EDC (411 mg, 2.14 mmol), HOBT (290 mg, 2.14 mmol) and triethylamine (300 □L, 2.14 mmol) were added. After stirring for an additional 20 h the reaction mixture was washed with 6 mL portions of: 10% $KHSO_4$, water, saturated $NaHCO_3$, and saturated NaCl. The organic extracts were dried over $Na_2SO_4$, filtered and concentrated to afford 1.44 g of tert-butyl 4-(4-chloro-3-cyanobenzoyl)piperazine-1-carboxylate as a beige solid.

tert-butyl 4-(3-(aminomethyl)-4-chlorobenzyl)piperazine-1-carboxylate. To a 250 mL round-bottom flask fitted with a reflux condenser, rubber septum and stir bar under a positive pressure of $N_2$ was added 10.3 mL of 1M $BH_3$.THF complex in THF. This mixture was cooled in an ice bath. The tert-butyl 4-(4-chloro-3-cyanobenzoyl)piperazine-1-carboxylate (1.44 g, 4.12 mmol) was dissolved in 20 mL of THF and added dropwise to the reaction mixture via syringe. The ice bath was removed, replaced with a heating mantle and the reaction mixture was heated at reflux for 20 h. The reaction was cooled to RT and to the mixture was added 48 mL of 20% HOAc in water (v/v) and the mixture was stirred between pH 3-4 for 20 h. The mixture was concentrated to half its original volume with a rotary evaporator and then diluted with 20 mL of 10% citric acid. This mixture was washed once with 25 mL of EtOAc and the aqueous layer was brought to pH=11 by the addition of 52 mL of 3N NaOH. The resultant mixture was extracted with EtOAc (3×40 mL). The combined extracts were washed with 40 mL of saturated NaCl solution. The organic layer was dried over $Na_2SO_4$, filtered and concentrated to give 1.00 g of tert-butyl 4-(3-(aminomethyl)-4-chlorobenzyl)piperazine-1-carboxylate as a pale yellow oil.

tert-butyl 4-(4-chloro-3-((3-(6-methylpyridin-3-yl)ureido)methyl)benzyl)piperazine-1-carboxylate. The tert-butyl 4-(3-(aminomethyl)-4-chlorobenzyl)piperazine-1-carboxylate from Step 2 (990 mg, 2.91 mmol) was dissolved in 8 mL of $CH_2Cl_2$ and maintained under a positive nitrogen pressure.

3-Isocyanato-6-methylpyridine (430 mg, 3.20 mmol) was dissolved in 8 mL of $CH_2Cl_2$ and added dropwise to the tert-butyl 4-(3-(aminomethyl)-4-chlorobenzoyl)piperazine-1-carboxylate solution via syringe. After 15 min, triethylamine was added (410 □L, 2.91 mmol) and stirring was continued for an additional 45 min. After this time the reaction was filtered through a cotton plug to remove the insoluble bis-pyridyl urea. The filtrate was washed with 6 mL portions of water and saturated NaCl solution. The organic layer was dried over $Na_2SO_4$, filtered and concentrated to afford 1.41 g of a white foam. This material was purified on a silica pad (9.5 cm in diameter, 6 cm high) in a 600 mL fritted glass funnel. Elution was as follows: 1 L of methanol-EtOAc-triethylamine (5:94:1 v/v), 500 mL methanol-EtOAc (10:90 to 25:75 v/v). 250-mL fractions were collected. 958 mg of tert-butyl 4-(4-chloro-3-((3-(6-methylpyridin-3-yl)ureido)methyl)benzyl)piperazine-1-carboxylate as a colorless oil was obtained. TLC methanol-EtOAc-triethylamine (10:89:1 v/v) $R_f$=0.28.

1-(2-chloro-5-(piperazin-1-ylmethyl)benzyl)-3-(6-methylpyridin-3-yl)urea trihydrochloride salt. The tert tert-butyl 4-(4-chloro-3-((3-(6-methylpyridin-3-yl)ureido)methyl)benzyl)piperazine-1-carboxylate from above (954 mg, 2.01 mmol) was dissolved in 40 mL of methanol and treated with 10 mL of 4N HCl in dioxane (40.2 mmol) with stirring for 16 h. The solvents were removed to afford 1.13 g of 1-(2-chloro-5-(piperazin-1-ylmethyl)benzyl)-3-(6-methylpyridin-3-yl) urea trihydrochloride salt as a white solid.

1-(2-chloro-5-((4-(methylsulfonyl)piperazin-1-yl)methyl)benzyl)-3-(6-methylpyridin-3-yl)urea. In a 20 mL scintillation vial equipped with a stir bar, 1-(2-chloro-5-(piperazin-1-ylmethyl)benzyl)-3-(6-methylpyridin-3-yl)urea hydrochloride salt (367 mg, 654 □mol) and DMAP (2 mg) were sealed with a septum cap and maintained under a positive nitrogen pressure. To the mixture was added 6 mL of anyhydrous $CH_2Cl_2$, followed by DIPEA (520 □L, 2.94 mmol) and methanesulfonyl chloride (70 □L, 785 □mol). The reaction mixture was stirred for 16 h. The reaction mixture was diluted with 6 mL of EtOAc. The organic solution was washed with 4 mL each of water and saturated NaCl solution, dried over $Na_2SO_4$, filtered and concentrated to afford 1-(2-chloro-5-((4-(methylsulfonyl)piperazin-1-yl)methyl)benzyl)-3-(6-methylpyridin-3-yl)urea as beige foam (209 mg).

Example 2

Methyl 4-(2-(difluoromethoxy)-5-((3-(6-methylpyridin-3-yl)ureido)methyl)benzyl)piperazine-1-carboxylate tert-butyl 4-(2-hydroxy-5-iodobenzoyl)piperazine-1-carboxylate. Performed identical to tert-butyl 4-(4-chloro-3-cyanobenzoyl)piperazine-1-carboxylate in Example 1 except 2-hydroxy-5-iodobenzoic acid was used in place of 3-cyano-4-chlorobenzoic acid.

tert-butyl 4-(2-(difluoromethoxy)-5-iodobenzoyl)piperazine-1-carboxylate. A stirred slurry of tert-butyl 4-(2-hydroxy-5-iodobenzoyl)piperazine-1-carboxylate (7.06 g, 16.33 mmol) and potassium hydroxide (30% aqueous, 120 mL) in 2-propanol (200 mL) at 50° C. was treated with chlorodifluoromethane by bubbling a stream of the gaseous reagent through the stirring reaction mixture for 6 min. The reaction mixture was placed in a Parr high pressure reaction vessel, heated at 80° C. for 16 h and then cooled to ambient temperature. The resulting solution was concentrated to remove 2-propanol and the aqueous portion was extracted with ethyl acetate (3×200 mL). The organic portions were dried ($Na_2SO_4$) and concentrated. The residue was purified by reverse phase HPLC to give 5.55 g of tert-butyl 4-(2-(difluoromethoxy)-5-iodobenzoyl)piperazine-1-carboxylate as a white solid.

tert-butyl 4-(5-cyano-2-(difluoromethoxy)benzoyl)piperazine-1-carboxylate. In a 250 mL round-bottom flask tert-butyl 4-(2-hydroxy-5-iodobenzoyl)piperazine-1-carboxylate (5.55 g, 11.5 mmol), $Zn(CN)_2$ (2.06 g, 17.2 mmol) and $Pd(PPh_3)_4$ (1.31 g, 1.15 mmol) were suspended in 93 mL of anhydrous DMF under a positive nitrogen pressure. The reaction mixture was heated for 16 h at 70° C. After this time the addition of the cyanide source and catalyst were repeated. After an additional 16 h of reaction time the mixture was diluted with 280 mL of water and extracted with EtOAc (3×125 mL). The combined organic extracts were dried over $Na_2SO_4$, filtered and concentrated to afford 5.76 g of a brown oil. The oil was purified by reverse-phase HPLC to afford 2.90 g of tert-butyl 4-(5-cyano-2-(difluoromethoxy)benzoyl) piperazine-1-carboxylate as a white foam.

Methyl 4-(2-(difluoromethoxy)-5-((3-(6-methylpyridin-3-yl)ureido)methyl)benzyl)piperazine-1-carboxylate. The tert-butyl 4-(5-cyano-2-(difluoromethoxy)benzoyl)piperazine-1-carboxylate from above was converted to methyl 4-(2-(difluoromethoxy)-5-((3-(6-methylpyridin-3-yl)ureido)methyl)benzyl)piperazine-1-carboxylate by method is similar to those used in example 1.

Example 3

Ethyl 4-(4-fluoro-3-((3-(3-methylisoxazol-5-yl)ureido)methyl)benzyl)piperazine-1-carboxylate tert-butyl 4-(3-cyano-4-fluorobenzyl)piperazine-1-carboxylate: 2-Fluoro-5-formylbenzonitrile (25 g, 167.6 mmol, 1.0 equiv.) was dissolved in $CH_2Cl_2$ (450 mL) at RT. To this solution was added tert-butyl piperazine-1-carboxylate (31.2 g, 167.6 mmol, 1 equiv.) followed by the portion-wise addition of sodium triacetoxyborohydride (49.7 g, 234.6 mmol, 1.4 equiv.). The reaction vessel was placed under an atmosphere of nitrogen and allowed to stir at room temperature for 1 hour. Saturated $NaHCO_3$ was added and the resultant mixture stirred for 10 minutes. The mixture was concentrated under reduced pressure, diluted with EtOAc (700 mL), and extracted into IN $KHSO_4$ (3×150 mL). The aqueous layer was basified to pH 10 using 50% NaOH solution, saturated with NaCl, extracted into DCM (2×100 mL) and EtOAc (1×200 mL), and dried over $Na_2SO_4$. Concentration in vacuo resulted in the isolation of 10.2 g of tert-butyl 4-(3-cyano-4-fluorobenzyl)piperazine-1-carboxylate.

Ethyl 4-(3-cyano-4-fluorobenzyl)piperazine-1-carboxylate. The tert-butyl 4-(3-cyano-4-fluorobenzyl)piperazine-1-carboxylate from the previous step (15.0 g, 47.0 mmol, 1.0 equiv.) was dissolved in $CH_2Cl_2$ (150 mL), to which TFA (150 mL) was slowly added and the resultant mixture stirred for 10 minutes. $CH_2Cl_2$ and TFA were removed by concentration in vacuo. The resulting residue was dissolved in THF (170 mL) and $Et_3N$ (Aldrich, redistilled, 16.6 mL, 188.1 mmol, 4.0 equiv.). The reaction vessel was cooled to 0° C. and ethyl chloroformate (Aldrich, 4.7 mL, 49.4 mmol, 1.05 equiv.) was added dropwise via syringe under a nitrogen atmosphere. After 30 minutes the reaction was concentrated under reduced pressure, diluted with EtOAc, washed with sat. aq. $NaHCO_3$ and brine, and dried over $Na_2SO_4$. The organic layer was removed in vacuo to yield 5.9 g of ethyl 4-(3-cyano-4-fluorobenzyl)piperazine-1-carboxylate.

Ethyl 4-(3-(aminomethyl)-4-fluorobenzyl)piperazine-1-carboxylate. Ethyl 4-(3-cyano-4-fluorobenzyl)piperazine-1-carboxylate (5.9 g, 20.3 mmol, 1.0 equiv.) was dissolved in MeOH (47 mL), to which was added 12 M HCl (2.0 mL, 24.3 mmol, 1.2 equiv) while stirring vigorously. A catalytic amount of palladium on carbon (Aldrich, wet, 10% w/w) was then added as a MeOH slurry. The reaction was placed in a Parr bomb under atmosphere of $H_2$ (55 psi) for 1 hour at room temperature. The reaction mixture was filtered through Celite and concentrated under reduced pressure to provide 5 g of ethyl 4-(3-(aminomethyl)-4-fluorobenzyl)piperazine-1-carboxylate.

Ethyl 4-(4-fluoro-3-((3-(3-methylisoxazol-5-yl)ureido)methyl)benzyl)piperazine-1-carboxylate. 5-Amino-3-methyl-isoxazole (100 mg, 1.02 mmol, 1.0 equiv.) was added to a vial and dissolved in anhydrous THF (EMD, 5 mL) and redistilled DIPEA (196 ul, 1.12 mmol, 1.1 equiv.) under atmosphere of $N_2$. To this solution 4-nitrophenyl chloroformate (205 mg, 1.02 mmol, 1.0 equiv.) was added directly and the vial was purged again with nitrogen. After 10 minutes, the reaction turned off-white and opaque; after 12 hours of stirring at room temperature the mixture became yellow in color. The presence of the intermediate carbamate was confirmed by TLC (10% MeOH/DCM) and reverse phase LC/MS: a strong UV peak was observed but the mass was not observed in positive ionization mode. Ethyl 4-(3-(aminomethyl)-4-fluorobenzyl)piperazine-1-carboxylate (139 mg, 1.02 mmol, 1.0 equiv.) in a minimal amount of THF/DCM and added drop-wise to the reaction vessel under atmosphere of $N_2$. The mixture was stirred for 1 hour then heated to 65° C. for 2 hours. The reaction was allowed to cool to room temperature and then diluted with ethyl acetate (30 mL), washed with 1N NaOH (2×10 mL) and brine (1×10 mL), and dried over $Na_2SO_4$. The organic layer was then concentrated under reduced pressure to yield a yellow oil. The yellow oil was loaded onto a Biotage samplet and purified via automated silica gel chromatography in MeCN/DCM (Linear gradient from 15% to 74% [300 mL], held at 74%[140 mL], linear gradient from 74% to 100% [300 mL], and held at 100% [400 mL]) to provide 24 mg of ethyl 4-(4-fluoro-3-((3-(3-methyl-isoxazol-5-yl)ureido)methyl)benzyl)piperazine-1-carboxylate.

Example 4

(S)-N,N-dimethyl-4-(3-(1-(3-(6-methylpyridin-3-yl)ureido)ethyl)benzyl)piperazine-1-sulfonamide tert-butyl 4-(3-acetylbenzoyl)piperazine-1-carboxylate. 3-Acetylbenzoic acid (1.64 g, 10.0 mmol), 1-tert-butoxycarbonylpiperazine (2.23 g, 12.0 mmol), HATU (4.56 g, 12.0 mmol) and HOAT (1.63 g, 12.0 mmol) were dissolved in 20 mL anhydrous DMF in a 100 mL round-bottom flask under a positive pressure of $N_2$ in an ice bath. DIPEA (3.8 mL, 22.0 mmol) was added and the mixture stirred at ambient temperature for 2 h. The solution was diluted with 100 mL of EtOAc and washed with 40 mL each: 0.2 N NaOH solution once and saturated NaCl solution twice. The organic layer was dried over $Na_2SO_4$, filtered, concentrated and purified by silica gel chromatography using EtOAc-hexanes (2:1 v/v) as the eluant to give tert-butyl 4-(3-acetylbenzoyl)piperazine-1-carboxylate as 2.97 g of white solid.

(S)-tert-butyl 4-(3-(1-hydroxyethyl)benzyl)piperazine-1-carboxylate. Under a positive pressure of $N_2$ 1-1.5M solution of (S)-Methyl oxazaborolidine (0.5 mL, 5.0 mmol) was diluted in 2 mL of toluene and treated with 3.6 mL of borane-N,N-diethylaniline. The tert-butyl 4-(3-acetylbenzoyl)piperazine-1-carboxylate from above in 3 mL of anhydrous toluene was added to the above solution over 1 hour and stirred for an additional hour. The mixture was stirred at 20° C. for another hour. To the mixture was added 6 mL MeOH, 12 mL 1N HCl and the resultant mixture stirred for 20 min. The mixture was diluted with 50 mL toluene and washed with saturated NaCl (50 mL). The organic extracts were dried over $Na_2SO_4$, filtered and concentrated at reduced pressure. The residue was heated at reflux in $Et_2NH$ for 1 hour. Purification by reverse-phase HPLC to afforded (S)-tert-butyl 4-(3-(1-hydroxyethyl)benzyl)piperazine-1-carboxylate as 1.08 g of white solid.

(S)-tert-butyl 4-(3-(1-(1,3-dioxoisoindolin-2-yl)ethyl)benzyl)piperazine-1-carboxylate. To a solution of (S)-tert-butyl 4-(3-(1-hydroxyethyl)benzyl)piperazine-1-carboxylate (480 mg, 1.50 mmol) in 10 mL of anhydrous THF at 0° C. under a positive pressure of $N_2$ were added phthalimde (330 mg, 2.25 mmol), triphenyl phosphine (590 mg, 2.25 mmol) and DIAD (440 □L, 2.25 mmol). The solution was warmed up to ambient temperature and stirred 1 h. The solvent was removed at reduced pressure and the residue was purified by reverse-phase HPLC to afford (S)-tert-butyl 4-(3-(1-(1,3-dioxoisoindolin-2-yl)ethyl)benzyl)piperazine-1-carboxylate as 490 mg of a white solid.

(S)-tert-butyl 4-(3-(1-aminoethyl)benzyl)piperazine-1-carboxylate. The (S)-tert-butyl 4-(3-(1-(1,3-dioxoisoindolin-2-yl)ethyl)benzyl)piperazine-1-carboxylate from the previous step (490 mg, 1.09 mmol) was dissolved in 5 mL hydrazine and stirred at ambient temperature for 16 h. The solvent was removed at reduced pressure and the resulting (S)-tert-butyl 4-(3-(1-aminoethyl)benzyl)piperazine-1-carboxylate was used in the next step without additional purification.

(S)-tert-butyl 4-(3-(1-(3-(6-methylpyridin-3-yl)ureido)ethyl)benzyl)piperazine-1-carboxylate. (S)-tert-butyl 4-(3-(1-(3-(6-methylpyridin-3-yl)ureido)ethyl)benzyl)piperazine-1-carboxylate was synthesized in a manner analogous to tert-butyl 4-(4-chloro-3-((3-(6-methylpyridin-3-yl)ureido)methyl)benzyl)piperazine-1-carboxylate in example 1.

(S)-1-(6-methylpyridin-3-yl)-3-(1-(3-(piperazin-1-ylmethyl)phenyl)ethyl)urea trihydrochloride salt. (S)-1-(6-methylpyridin-3-yl)-3-(1-(3-(piperazin-1-ylmethyl)phenyl)ethyl)urea trihydrochloride salt was synthesized in a manner analogous to 1-(2-chloro-5-(piperazin-1-ylmethyl)benzyl)-3-(6-methylpyridin-3-yl)urea trihydrochloride salt in example 1.

(S)-N,N-dimethyl-4-(3-(1-(3-(6-methylpyridin-3-yl)ureido)ethyl)benzyl)piperazine-1-sulfonamide. (S)-N,N-dimethyl-4-(3-(1-(3-(6-methylpyridin-3-yl)ureido)ethyl)benzyl)piperazine-1-sulfonamide was synthesized in a manner analogous to 1-(2-chloro-5-((4-(methylsulfonyl)piperazin-1-yl)methyl)benzyl)-3-(6-methylpyridin-3-yl)urea in Example 1 except that N,N-dimethylsulfamoyl chloride was used as the electrophile instead of methanesulfonyl chloride.

Example 5

Using the methods similar to those described herein, the following compounds were prepared and assayed for activity.

| Compound | MS Data | Comments |
| --- | --- | --- |
| ({3-[((2S)-4-acetyl-2-methylpiperazinyl)methyl]-2-fluorophenyl}amino)-N-(6-methyl(3-pyridyl))carboxamide | 400.2 | (M + H)+ |

| Compound | MS Data | Comments |
|---|---|---|
| [(6-acetyl(3-pyridyl))amino]-N-[(5-{4-(ethylsulfonyl)piperazinyl]methyl}-2-fluorophenyl)methyl]carboxamide | 478.1 | (M + H)+ |
| [(6-cyano(3-pyridyl))amino]-N-[(5-{4-(ethylsulfonyl)piperazinyl]methyl}-2-fluorophenyl)methyl]carboxamide | 461.1 | (M + H)+ |
| [(6-methyl(3-pyridyl))amino]-N-[(2-methyl-5-{[4-(2-methylpropanoyl)piperazinyl]methyl}phenyl)methyl]carboxamide | 482 | (M + Na)+ |
| [(6-methyl(3-pyridyl))amino]-N-[(2-methyl-5-{[4-(methylsulfonyl)piperazinyl]methyl}phenyl)methyl]carboxamide | 432 | (M + H)+ |
| [(6-methyl(3-pyridyl))amino]-N-{[2-methyl-5-({4-[(methylethyl)sulfonyl]piperazinyl}methyl)phenyl]methyl}carboxamide | 446 | (M + Na)+ |
| {(3R)-3-[5-fluoro-3-({[(6-methyl(3-pyridyl))amino]carbonylamino}methyl)-phenoxy]piperidyl}-N,N-dimethylcarboxamide | | |
| ethyl 4-[(4-fluoro-3-{[(pyrimidin-5-ylamino)carbonylamino]methyl}phenyl)-methyl]piperazinecarboxylate | 417.1 | (M + H)+ |
| ethyl 4-{[2-(difluoromethoxy)-5-({[(6-methyl(3-pyridyl))amino]carbonylamino}methyl)phenyl]methyl}piperazinecarboxylate | 478.2 | (M + H)+ |
| ethyl 4-{[2,4-difluoro-3-({[(6-methyl(3-pyridyl))amino]carbonylamino}methyl)phenyl]methyl}piperazinecarboxylate | 448.1 | (M + H)+ |
| ethyl 4-{[3-({[(6-acetyl(3-pyridyl))amino]-carbonylamino}methyl)-4-fluorophenyl]methyl}-piperazinecarboxylate | 458.1 | (M + H)+ |
| ethyl 4-{[3-({[(6-cyano(3-pyridyl))amino]-carbonylamino}methyl)-4-fluorophenyl]methyl}-piperazinecarboxylate | 441.1 | (M + H)+ |
| ethyl 4-{[4-(difluoromethoxy)-3-({[(6-methyl(3-pyridyl))amino]carbonylamino}methyl)phenyl]methyl}piperazinecarboxylate | 478.2 | (M + H)+ |
| ethyl 4-{[4-fluoro-3-({[(2-methylpyrimidin-5-yl)amino]carbonylamino}methyl)phenyl]methyl}piperazmecarboxylate | 431.1 | (M + H)+ |
| ethyl 4-{[4-fluoro-3-({[(3-methylisoxazol-5-yl)amino]carbonylamino}methyl)phenyl]-methyl}piperazinecarboxylate | 420.1 | (M + H)+ |
| ethyl 4-{[4-fluoro-3-({[(6-methoxy(3-pyridyl))amino]carbonylamino}methyl)phenyl]-methyl}piperazinecarboxylate | 446.1 | (M + H)+ |
| ethyl 4-{[4-fluoro-3-({[(6-methyl(3-pyridyl))amino]carbonylamino}methyl)phenyl]-methyl}piperazmecarboxylate | 430.2 | (M + H)+ |
| ethyl 4-{[4-methyl-3-({[(6-methyl(3-pyridyl))amino]carbonylamino}methyl)phenyl]-methyl}piperazinecarboxylate | 426 | (M + H)+ |
| methyl (3R)-3-[5-fluoro-3-({[(6-methyl(3-pyridyl))amino]carbonylamino}methyl)phenoxy]-piperidinecarboxylate | | |
| methyl 4-{[2,4-difluoro-3-({[(6-methyl(3-pyridyl))amino]carbonylamino}methyl)phenyl]-methyl}piperazinecarboxylate | 434.1 | (M + H)+ |
| methyl 4-{[2-chloro-5-({[(6-methyl(3-pyridyl))amino]carbonylamino}methyl)phenyl]-methyl}piperazinecarboxylate | 432 | (M + H)+ |
| methyl 4-{[2-fluoro-3-({[(6-methyl(3-pyridyl))amino]carbonylamino}methyl)phenyl]-methyl}piperazinecarboxylate | 416.1 | (M + H)+ |
| methyl 4-{[2-fluoro-5-({[(6-methyl(3-pyridyl))amino]carbonylamino}methyl)phenyl]-methyl}piperazinecarboxylate | 416.1 | (M + H)+ |
| methyl 4-{[2-methyl-5-({[(6-methyl(3-pyridyl))amino]carbonylamino}methyl)phenyl]-methyl}piperazinecarboxylate | 432 | (M + H)+ |
| methyl 4-{[3-({[(6-methyl-3-pyridyl)amino]carbonylamino}methyl)phenyl]-methyl}piperazinecarboxylate | 398.1 | (M + H)+ |
| methyl 4-{[4-difluoromethoxy-3-({[(6-methyl(3-pyridyl))amino]carbonylamino}methyl)phenyl]methyl}piperazinecarboxylate | 464 | (M + H)+ |
| methyl 4-{[4-chloro-3-({[(6-methyl(3-pyridyl))amino]carbonylamino}methyl)phenyl]methyl}piperazinecarboxylate | 495.1 | (M + H)+ |
| methyl 4-{[4-fluoro-3-({[(6-methyl(3-pyridyl))amino]carbonylamino}methyl)phenyl]-methyl}piperazinecarboxylate | 416.1 | (M + H)+ |
| methyl 4-{[4-methyl-3-({[(6-methyl(3-pyridyl))amino]carbonylamino}methyl)phenyl]methyl}piperazinecarboxylate | 412 | (M + H)+ |
| methyl 4-{2-[3-({[(6-methyl-3-pyridyl)amino]carbonylamino}methyl)phenyl]ethyl}piperazinecarboxylate | | |
| methylethyl 4-{[4-fluoro-3-({[(6-methyl(3-pyridyl))amino]carbonylamino}methyl)phenyl]methyl}piperazinecarboxylate | 444.2 | (M + H)+ |
| methylethyl 4-{[4-methyl-3-({[(6-methyl(3-pyridyl))amino]carbonylamino}methyl)phenyl]methyl}piperazinecarboxylate | 440 | (M + H)+ |
| N-({3-[(3R)-1-(methylsulfonyl)(3-piperidyloxy)]-5-fluorophenyl}methyl)[(6-methyl(3-pyridyl))amino]carboxamide | | |
| N-({3-[(4-acetylpiperazinyl)methyl]-2,6-difluorophenyl}methyl)[(6-methyl(3-pyridyl))-amino]carboxamide | 418.1 | (M + H)+ |
| N-({3-[(4-acetylpiperazinyl)methyl]-4-chlorophenyl}methyl)[(6-methyl(3-pyridyl))amino]-carboxamide | 416 | (M + H)+ |
| N-({3-[(4-acetylpiperazinyl)methyl]-4-fluorophenyl}methyl)[(6-methyl(3-pyridyl))amino]carboxamide | 400.1 | (M + H)+ |
| N-({3-[(4-acetylpiperazinyl)methyl]-4-methyl-phenyl}methyl)[(6-methyl(3-pyridyl))amino]-carboxamide | 416 | (M + H)+ |
| N-({3-[(4-acetylpiperazinyl)methyl]-5-methyl-phenyl}methyl)[(6-methyl(3-pyridyl))amino]-carboxamide | 396.3 | (M + H)+ |
| N-({3-[(4-acetylpiperazinyl)methyl]phenyl}-methyl)[(6-methyl(3-pyridyl))amino]carboxamide | 382.1 | (M + H)+ |
| N-({3-[2-(4-acetylpiperazinyl)ethyl]phenyl}-methyl)[(6-methyl(3-pyridyl))amino]carboxamide | | |
| N-({4-[(4-acetylpiperazinyl)methyl](2-pyridyl)}-methyl)[(6-methyl(3-pyridyl))amino]carboxamide | | |
| N-({4-chloro-3-[(4-cyanopiperazinyl)methyl]-phenyl}methyl)[(6-methyl(3-pyridyl))amino]-carboxamide | 400 | (M + H)+ |
| N-({5-[(4-acetylpiperazinyl)methyl]-2-fluoro-phenyl}methyl)[(6-methyl(3-pyridyl))amino]-carboxamide | 400.1 | (M + H)+ |
| N-({5-[(4-acetylpiperazinyl)methyl]-2-methyl-phenyl}methyl)[(6-methyl(3-pyridyl))amino]-carboxamide | 396 | (M + H)+ |
| N-({5-chloro-3-[(4-cyanopiperazinyl)methyl]-phenyl}methyl)[(6-methyl(3-pyridyl))amino]-carboxamide | 400 | (M + H)+ |
| N-[(2,6-difluoro-3-{[4-(methylsulfonyl)piperazinyl]methyl}phenyl)methyl][(6-methyl(3-pyridyl))amino]-carboxamide | 454.1 | (M + H)+ |
| N-[(2-chloro-5-{[4-(ethylsulfonyl)piperazinyl]methyl}phenyl)methyl]-[(6-methyl(3-pyridyl))amino]carboxamide | 466.1 | (M + H)+ |
| N-[(2-chloro-5-{[4-(methylsulfonyl)piperazinyl]methyl}phenyl)-methyl][(6-methyl(3-pyridyl))amino]carboxamide | 452.2 | (M + H)+ |
| N-[(2-fluoro-5-{[4-(3-methylbutanoyl)piperazinyl]methyl]phenyl}methyl][(6-methyl(3-pyridyl))amino]carboxamide | 442.2 | (M + H)+ |
| N-[(2-fluoro-5-{[4-(methylsulfonyl)piperazinyl]methyl}phenyl)-methyl][(6-methyl(3-pyridyl))amino]carboxamide | 436.1 | (M + H)+ |
| N-[(2-fluoro-5-{[4-(propylsulfonyl)piperazinyl]methyl}phenyl)-methyl][(6-methyl(3-pyridyl))amino]carboxamide | 464.1 | (M + H)+ |
| N-[(3-{[4-(ethylsulfonyl)piperazinyl]methyl}-2,6-difluorophenyl)methyl][(6-methyl(3-pyridyl))amino]carboxamide | 468.1 | (M + H)+ |

-continued

| Compound | MS Data | Comments |
|---|---|---|
| N-[(3-{[4-(ethylsulfonyl)piperazinyl]methyl}-4-fluorophenyl)methyl][(6-methyl(3-pyridyl))amino]carboxamide | 450.1 | (M + H)+ |
| N-[(3-{[4-(ethylsulfonyl)piperazinyl]methyl}-4-methylphenyl)methyl][(6-methyl(3-pyridyl))amino]carboxamide | 466 | (M + H)+ |
| N-[(3-{[4-(ethylsulfonyl)piperazinyl]methyl}-5-fluorophenyl)methyl][(6-methyl(3-pyridyl))amino]carboxamide | 450.2 | (M + H)+ |
| N-[(3-{[4-(ethylsulfonyl)piperazinyl]methyl}-5-methylphenyl)methyl][(6-methyl(3-pyridyl))amino]carboxamide | 446.2 | (M + H)+ |
| N-[(3-{[4-(ethylsulfonyl)piperazinyl]methyl}-phenyl)methyl][(6-methyl(3-pyridyl))amino]carboxamide | 432.1 | (M + H)+ |
| N-[(3-{[4-(N,N-dimethylcarbamoyl)piperazinyl]methyl}-4-chlorophenyl)methyl][(6-methyl(3-pyridyl))amino]carboxamide | 444 | (M + H)+ |
| N-[(3-{[4-(N,N-dimethylcarbamoyl)piperazinyl]methyl}-4-fluorophenyl)methyl][(6-methyl(3-pyridyl))amino]carboxamide | 429.2 | (M + H)+ |
| N-[(3-{2-[4-(ethylsulfonyl)piperazinyl]ethyl}phenyl)methyl][(6-methyl(3-pyridyl))amino]carboxamide | | |
| N-[(3-fluoro-6-{[4-(methylsulfonyl)piperazinyl]methyl}(2-pyridyl))methyl][(6-methyl(3-pyridyl))amino]carboxamide | | |
| N-[(4-(difluoromethoxy)-3-{[4-(ethylsulfonyl)piperazinyl]methyl}phenyl)methyl]-[(6-methyl(3-pyridyl))amino]carboxamide | 499 | (M + H)+ |
| N-[(4-(difluoromethoxy)-3-{[4-(methylsulfonyl)piperazinyl]methyl}phenyl)-methyl][(6-methyl(3-pyridyl))amino]carboxamide | 484 | (M + H)+ |
| N-[(4-{[4-(ethylsulfonyl)piperazinyl]methyl}(2-pyridyl))methyl][(6-methyl(3-pyridyl))amino]carboxamide | | |
| N-[(4-chloro-3-{[4-(ethylsulfonyl)piperazinyl]methyl}phenyl)methyl][(6-methyl(3-pyridyl))amino]carboxamide | 466 | (M + H)+ |
| N-[(5-{[4-(2,2-dimethylpropanoyl)piperazinyl]methyl}-2-fluorophenyl)methyl][(6-methyl(3-pyridyl))amino]carboxamide | 442.2 | (M + H)+ |
| N-[(5-{[4-(ethylsulfonyl)piperazinyl]methyl}-2-fluorophenyl)methyl][(6-methyl(3-pyridyl))amino]carboxamide | 450.1 | (M + H)+ |
| N-[(5-{[4-(ethylsulfonyl)piperazinyl]methyl}-2-fluorophenyl)methyl][(6-methoxy(3-pyridyl))amino]carboxamide | 466.1 | (M + H)+ |
| N-[(5-{[4-(ethylsulfonyl)piperazinyl]methyl}-2-fluorophenyl)methyl](pyrimidin-5-ylamino)carboxamide | 437.1 | (M + H)+ |
| N-[(5-{[4-(ethylsulfonyl)piperazinyl]methyl}-2-fluorophenyl)methyl][(2-methylpyrimidin-5-yl)amino]carboxamide | 451.1 | (M + H)+ |
| N-[(5-{[4-(ethylsulfonyl)piperazinyl]methyl}-2-fluorophenyl)methyl][(6-methoxy(3-pyridyl))amino]carboxamide | | |
| N-[(5-{[4-(ethylsulfonyl)piperazinyl]methyl}-2-fluorophenyl)methyl][(6-methyl(3-pyridyl))amino]carboxamide | | |
| N-[(5-{[4-(ethylsulfonyl)piperazinyl]methyl}-2-methylphenyl)methyl][(6-methyl(3-pyridyl))amino]carboxamide | 468 | (M + Na)+ |
| N-[(5-{[4-(N,N-dimethylcarbamoyl)piperazinyl]methyl}-2-fluorophenyl)methyl][(6-methyl(3-pyridyl))amino]carboxamide | 429.2 | (M + H)+ |
| N-[4-({4-[(dimethylamino)sulfonyl]piperazinyl}methyl)-3-fluoro(2-pyridyl)][(6-methyl(3-pyridyl))amino]carboxamide | | |
| N-{(1S)-1-[3-({4-[(dimethylamino)sulfonyl]piperazinyl}methyl)phenyl]ethyl}[(6-methyl(3-pyridyl))amino]carboxamide | 461.2 | (M + H)+ |
| N-{[2-chloro-5-(piperazinylmethyl)phenyl]methyl}[(6-methyl(3-pyridyl))amino]carboxamide | 374.1 | (M + H)+ |
| N-{[2-fluoro-5-({4-[(methylethyl)sulfonyl]piperazinyl}methyl)phenyl]methyl}[(6-methyl(3-pyridyl))amino]carboxamide | 464.1 | (M + H)+ |
| N-{[3-((3R)-1-acetyl(3-piperidyloxy))-5-fluorophenyl]ethyl}(3-pyridylamino)carboxamide | | |
| N-{[3-((3R)-1-acetyl(3-piperidyloxy))-5-fluorophenyl]ethyl}[(6-methyl(3-pyridyl))amino]carboxamide | | |
| N-{[3-((3R)-1-acetyl(3-piperidyloxy))-5-fluorophenyl]methyl}[(6-ethynyl(3-pyridyl))amino]carboxamide | | |
| N-{[3-((3R)-1-acetyl(3-piperidyloxy))-5-fluorophenyl]methyl}[(6-ethyl(3-pyridyl))amino]carboxamide | | |
| N-{[3-((3R)-1-acetyl(3-piperidyloxy))-5-fluorophenyl]methyl}[(6-methoxy(3-pyridyl))amino]carboxamide | | |
| N-{[3-((3R)-1-acetyl(3-piperidyloxy))-5-fluorophenyl]methyl}[(6-methyl(3-pyridyl))amino]carboxamide | | |
| N-{[3-((3R)-1-formyl(3-piperidyloxy))-5-fluorophenyl]methyl}[(6-methyl(3-pyridyl))amino]carboxamide | | |
| N-{[3-({4-[(dimethylamino)sulfonyl]piperazinyl}methyl)-2,6-difluorophenyl]methyl}[(6-methyl(3-pyridyl))amino]carboxamide | 483.1 | (M + H)+ |
| N-{[3-({4-[(dimethylamino)sulfonyl]piperazinyl}methyl)-4-chlorophenyl]methyl}[(6-methyl(3-pyridyl))amino]carboxamide | 481 | (M + H)+ |
| N-{[3-({4-[(dimethylamino)sulfonyl]piperaziny}methyl)-4-fluorophenyl]methyl}[(6-methyl(3-pyridyl))amino]carboxamide | 465.1 | (M + H)+ |
| N-{[3-({4-[(dimethylamino)sulfonyl]piperaziny}methyl)-4-methylphenyl]methyl}[(6-methyl(3-pyridyl))amino]carboxamide | 481 | (M + H)+ |
| N-{[3-({4-[(dimethylamino)sulfonyl]piperazinyl}methyl)-5-chlorophenyl]methyl}[(6-methyl(3-pyridyl))amino]carboxamide | 481 | (M + H)+ |
| N-{[3-({4-[(dimethylamino)sulfonyl]piperazinyl}methyl)-5-methylphenyl]methyl}[(6-methyl(3-pyridyl))amino]carboxamide | 461.1 | (M + H)+ |
| N-{[3-({4-[(dimethylamino)sulfonyl]piperaziny}methyl)phenyl]methyl}[(6-methyl(3-pyridyl))amino]carboxamide | 447.1 | (M + H)+ |
| N-{[3-(2-{4-[(dimethylamino)sulfonyl]piperazinyl}ethyl)phenyl]methyl}[(6-methyl(3-pyridyl))amino]carboxamide | | |
| N-{[4-({4-[(dimethylamino)sulfonyl]piperazinyl}methyl)(2-pyridyl)]methyl}[(6-methyl(3-pyridyl))amino]carboxamide | | |
| N-{[4-({4-[(dimethylamino)sulfonyl]piperazinyl}methyl)phenyl]methyl}[(6-methyl(3-pyridyl))amino]carboxamide | | |
| N-{[5-({4-[(dimethylamino)sulfonyl]piperazinyl}methyl)-2-fluorophenyl]methyl}[(6-methyl(3-pyridyl))amino]carboxamide | 465.1 | (M + H)+ |
| N-{2-[3-((3R)-1-acetyl(3-piperidyloxy))-5-fluorophenyl]ethyl}(3-pyridylamino)carboxamide | | |
| N-{2-[3-((3R)-1-acetyl(3-piperidyloxy))-5-fluorophenyl]ethyl}[(6-methyl(3-pyridyl))amino]carboxamide | | |
| N-{2-[3-((3R)-1-acetyl(3-piperidyloxy))-5-fluorophenyl]ethyl}[(6-ethyl(3-pyridyl))amino]carboxamide | | |
| tert-butyl (3R)-3-(5-fluoro-3-{2-[(3-pyridylamino)carbonylamino]ethyl}phenoxy)-piperidinecarboxylate | | |
| tert-butyl 4-{2-({[(6-methyl-3-pyridyl)amino]carbonylamino}methyl)-4-pyridyl]methyl}piperazinecarboxylate | | |
| tert-butyl 4-{[2,4-difluoro-3-({[(6-methyl-3-pyridyl)amino]carbonylamino}methyl)phenyl]methyl}piperazinecarboxylate | 476.1 | (M + H)+ |
| tert-butyl 4-{[3-({[(6-methyl-3-pyridyl)amino]carbonylamino}methyl)phenyl]methyl}piperazinecarboxylate | 440.2 | (M + H)+ |

-continued

| Compound | MS Data | Comments |
|---|---|---|
| tert-butyl 4-{[4-chloro-3-({[(6-methyl(3-pyridyl))amino]carbonylamino}methyl)phenyl]methyl}piperazinecarboxylate | 474.1 | (M + H)+ |
| tert-butyl 4-{[4-fluoro-3-({[(6-methyl(3-pyridyl))amino]carbonylamino}methyl)phenyl]methyl}piperazinecarboxylate | 458.2 | (M + H)+ |
| tert-butyl 4-{2-[3-({[(6-methyl-3-pyridyl)amino]carbonylamino}methyl)phenyl]ethyl}piperazinecarboxylate | | |

Example 6

Target Identification Assays

Specificity assays: Specificity towards cardiac myosin is evaluated by comparing the effect of the chemical entity on actin-stimulated ATPase of a panel of myosin isoforms: cardiac, skeletal and smooth muscle, at a single 50 µM concentration or to multiple concentrations of the chemical entity.

Myofibril assays: To evaluate the effect of compounds on the ATPase activity of full-length cardiac myosin in the context of native sarcomere, skinned myofibril assays are performed. Rat cardiac myofibrils are obtained by homogenizing rat cardiac tissue in the presence of detergent. Such treatment removes membranes and majority of soluble cytoplasmic proteins but leaves intact cardiac sarcomeric acto-myosin apparatus. Myofibril preparations retain the ability to hydrolyze ATP in a $Ca^{++}$ controlled manner. ATPase activities of such myofibril preparations in the presence and absence of compounds are assayed at $Ca^{++}$ concentrations giving 50% and 100% of a maximal rate.

Example 7

In vitro Model of Dose Dependent Cardiac Myosin ATPase Modulation

Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1\times10^{4}$ M to $1\times10^{-8}$ M.

The protein components specific to this assay are bovine cardiac myosin subfragment-1 (typically 0.5 µM), bovine cardiac actin (14 µM), bovine cardiac tropomyosin (typically 3 µM), and bovine cardiac troponin (typically 3-8 µM). The exact concentrations of tropomyosin and troponin are determined empirically, by titration to achieve maximal difference in ATPase activity when measured in the presence of 1 mM EGTA versus that measured in the presence of 0.2 mM $CaCl_2$. The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration corresponding to 50% of maximal ATPase activity ($pCa_{50}$), so a preliminary experiment is performed to test the response of the ATPase activity to free calcium concentrations in the range of $1\times10^{-4}$ M to $1\times10^{-8}$ M. Subsequently, the assay mixture is adjusted to the $pCa_{50}$ (typically $3\times10^{-7}$ M). Assays are performed by first preparing a dilution series of test compound, each with an assay mixture containing potassium Pipes, $MgCl_2$, BSA, DTT, pyruvate kinase, lactate dehydrogenase, myosin subfragment-1, antifoam, EGTA, $CaCl_2$, and water. The assay is started by adding an equal volume of solution containing potassium Pipes, $MgCl_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation $y=Bottom+((Top-Bottom)/(1+((EC50/X)^{Hill})))$. The AC1.4 is defined as the concentration at which ATPase activity is 1.4-fold higher than the bottom of the dose curve.

Example 8

Myocyte Assays

A. Preparation of Adult Cardiac Ventricular Rat Myocytes. Adult male Sprague-Dawley rats are anesthetized with a mixture of isoflurane gas and oxygen. Hearts are quickly excised, rinsed and the ascending aorta cannulated. Continuous retrograde perfusion is initiated on the hearts at a perfusion pressure of 60 cm $H_2O$. Hearts are first perfused with a nominally $Ca^{2+}$ free modified Krebs solution of the following composition: 110 mM NaCl, 2.6 mM KCL, 1.2 mM $KH_2PO_4$ 7 $H_2O$, 1.2 mM $MgSO_4$, 2.1 mM $NaHCO_3$, 11 mM glucose and 4 mM Hepes (all Sigma). This medium is not recirculated and is continually gassed with $O_2$. After approximately 3 minutes the heart is perfused with modified Krebs buffer supplemented with 3.3% collagenase (169 µ/mg activity, Class II, Worthington Biochemical Corp., Freehold, N.J.) and 25 µM final calcium concentration until the heart becomes sufficiently blanched and soft. The heart is removed from the cannulae, the atria and vessels discarded and the ventricles are cut into small pieces. The myocytes are dispersed by gentle agitation of the ventricular tissue in fresh collagenase containing Krebs prior to being gently forced through a 200 µm nylon mesh in a 50 cc tube. The resulting myocytes are resuspended in modified Krebs solution containing 25 µm calcium. Myocytes are made calcium tolerant by addition of a calcium solution (100 mM stock) at 10 minute intervals until 100 µM calcium is achieved. After 30 minutes the supernatant is discarded and 30-50 ml of Tyrode buffer (137 mM NaCL, 3.7 mM KCL, 0.5 mM MgCL, 11 mM glucose, 4 mM Hepes, and 1.2 mM $CaCl_2$, pH 7.4) is added to cells. Cells are kept for 60 min at 37° C. prior to initiating experiments and used within 5 hrs of isolation. Preparations of cells are used only if cells first passed QC criteria by responding to a standard (>150% of basal) and isoproterenol (ISO; >250% of basal). Additionally, only cells whose basal contractility is between 3 and 8% are used in the following experiments.

B. Adult Ventricular Myocyte Contractility Experiments. Aliquots of Tyrode buffer containing myocytes are placed in perfusion chambers (series 20 RC-27NE; Warner Instruments) complete with heating platforms. Myocytes are allowed to attach, the chambers heated to 37° C., and the cells then perfused with 37° C. Tyrode buffer. Myocytes are field stimulated at 1 Hz in with platinum electrodes (20% above threshold). Only cells that have clear striations, and are quiescent prior to pacing are used for contractility experiments.

To determine basal contractility, myocytes are imaged through a 40× objective and using a variable frame rate (60-240 Hz) charge-coupled device camera, the images are digitized and displayed on a computer screen at a sampling speed of 240 Hz. [Frame grabber, myopacer, acquisition, and analysis software for cell contractility are available from IonOptix (Milton, Mass.).] After a minimum 5 minute basal contractility period, test compounds (0.01-15 µM) are perfused on the myocytes for 5 minutes. After this time, fresh Tyrode buffer is perfused to determine compound washout characteristics. Using edge detection strategy, contractility of the myocytes and contraction and relaxation velocities are continuously recorded.

C. Contractility Analysis: Three or more individual myocytes are tested per compound, using two or more different myocyte preparations. For each cell, twenty or more contractility transients at basal (defined as 1 min prior to compound infusion) and after compound addition, are averaged and compared. These average transients are analyzed to determine changes in diastolic length, and using the Ionwizard analysis program (IonOptix), fractional shortening (% decrease in the diastolic length), and maximum contraction and relaxation velocities (um/sec) are determined. Analyses of the individual cells are combined. Increase in fractional shortening over basal indicates potentiation of myocyte contractility.

D. Calcium Transient Analysis: Fura loading: Cell permeable Fura-2 (Molecular Probes) is dissolved in equal amounts of pluronic (Mol Probes) and FBS for 10 min at RT. A 1 µM Fura stock solution is made in Tyrode buffer containing 500 mM probenecid (Sigma). To load cells, this solution is added to myocytes at RT. After 10 min. the buffer is removed, the cells washed with Tyrode containing probenecid and incubated at RT for 10 min. This wash and incubation is repeated. Simultaneous contractility and calcium measurements are determined within 40 min. of loading.

Imaging: A test compound is perfused on cells. Simultaneous contractility and calcium transient ratios are determined at baseline and after compound addition. Cells are digitally imaged and contractility determined as described above, using that a red filter in the light path to avoid interference with fluorescent calcium measurements. Acquisition, analysis software and hardware for calcium transient analysis are obtained from IonOptix. The instrumentation for fluorescence measurement includes a xenon arc lamp and a Hyperswitch dual excitation light source that alternates between 340 and 380 wavelengths at 100 Hz by a galvo-driven mirror. A liquid filled light guide delivers the dual excitation light to the microscope and the emission fluorescence is determined using a photomultiplier tube (PMT). The fluorescence system interface routes the PMT signal and the ratios are recorded using the IonWizard acquisition program.

Analysis: For each cell, ten or more contractility and calcium ratio transients at basal and after compound addition, where averaged and compared. Contractility average transients are analyzed using the Ionwizard analysis program to determine changes in diastolic length, and fractional shortening (% decrease in the diastolic length). The averaged calcium ratio transients are analyzed using the Ionwizard analysis program to determine changes in diastolic and systolic ratios and the 75% time to baseline ($T_{75}$).

E. Durability: To determine the durability of response, myocytes are challenged with a test compound for 25 minutes followed by a 2 min. washout period. Contractility response is compared at 5 and 25 min. following compound infusion.

F. Threshold Potential: Myocytes are field stimulated at a voltage approximately 20% above threshold. In these experiments the threshold voltage (minimum voltage to pace cell) is empirically determined, the cell paced at that threshold and then the test compound is infused. After the compound activity is at steady state, the voltage is decreased for 20 seconds and then restarted. Alteration of ion channels corresponds to increasing or lowering the threshold action potential.

G. Hz Frequency: Contractility of myocytes is determined at 3 Hz as follows: a 1 min. basal time point followed by perfusion of the test compound for 5 min. followed by a 2 min. washout. After the cell contractility has returned completely to baseline the Hz frequency is decreased to 1. After an initial acclimation period the cell is challenged by the same compound. As this species, rat, exhibits a negative force frequency at 1 Hz, at 3 Hz the FS of the cell should be lower, but the cell should still respond by increasing its fractional shortening in the presence of the compound.

H. Additive with Isoproterenol: To demonstrate that a compound act via a different mechanism than the adrenergic stimulant isoproterenol, cells are loaded with fura-2 and simultaneous measurement of contractility and calcium ratios are determined. The myocytes are sequentially challenged with 5 µm a test compound, buffer, 2 nM isoproterenol, buffer, and a combination of a test compound and isoproterenol.

Example 9

In vitro Model of Dose Dependent Cardiac Myosin ATPase Modulation

Bovine and rat cardiac myosins are purified from the respective cardiac tissues. Skeletal and smooth muscle myosins used in the specificity studies are purified from rabbit skeletal muscle and chicken gizzards, respectively. All myosins used in the assays are converted to a single-headed soluble form (S1) by a limited proteolysis with chymotrypsin. Other sarcomeric components: troponin complex, tropomyosin and actin are purified from bovine hearts (cardiac sarcomere) or chicken pectoral muscle (skeletal sarcomere).

Activity of myosins is monitored by measuring the rates of hydrolysis of ATP. Myosin ATPase is very significantly activated by actin filaments. ATP turnover is detected in a coupled enzymatic assay using pyruvate kinase (PK) and lactate dehydrogenase (LDH). In this assay each ADP produced as a result of ATP hydrolysis is recycled to ATP by PK with a simultaneous oxidation of NADH molecule by LDH. NADH oxidation can be conveniently monitored by decrease in absorbance at 340 nm wavelength.

Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1 \times 10^{-4}$ M to $1 \times 10^{-8}$ M.

The protein components specific to this assay are bovine cardiac myosin subfragment-1 (typically 0.5 µM), bovine cardiac actin (14 µM), bovine cardiac tropomyosin (typically 3 µM), and bovine cardiac troponin (typically 3-8 µM). The exact concentrations of tropomyosin and troponin are determined empirically, by titration to achieve maximal difference in ATPase activity when measured in the presence of 1 mM EGTA versus that measured in the presence of 0.2 mM $CaCl_2$.

The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration corresponding to 50% of maximal ATPase activity ($pCa_{50}$), so a preliminary experiment is performed to test the response of the ATPase activity to free calcium concentrations in the range of $1\times10^{-4}$ M to $1\times10^{-8}$ M. Subsequently, the assay mixture is adjusted to the $pCa_{50}$ (typically $3\times10^{-7}$ M). Assays are performed by first preparing a dilution series of test compound, each with an assay mixture containing potassium Pipes, $MgCl_2$, BSA, DTT, pyruvate kinase, lactate dehydrogenase, myosin subfragment-1, antifoam, EGTA, $CaCl_2$, and water. The assay is started by adding an equal volume of solution containing potassium Pipes, $MgCl_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation y=Bottom+((Top-Bottom)/(1+((EC50/X)^Hill))). The AC1.4 is defined as the concentration at which ATPase activity is 1.4-fold higher than the bottom of the dose curve.

Ability of a compound to activate cardiac myosin is evaluated by the effect of the compound on the actin stimulated ATPase of S1 subfragment. Actin filaments in the assay are decorated with troponin and tropomyosin and Ca++ concentration is adjusted to a value that would result in 50% of maximal activation. S1 ATPase is measured in the presence of a dilution series of the compound. Compound concentration required for 40% activation above the ATPase rate measured in the presence of control (equivalent volume of DMSO) is reported as $AC_{40}$.

Example 10

In vivo Fractional Shortening Assay

A. Animals Male Sprague Dawley rats from Charles River Laboratories (275-350 g) are used for bolus efficacy and infusion studies. Heart failure animals are described below. They are housed two per cage and have access to food and water ad libitum. There is a minimum three-day acclimation period prior to experiments.

B. Echocardiography Animals are anesthetized with isoflurane and maintained within a surgical plane throughout the procedure. Core body temperature is maintained at 37° C. by using a heating pad. Once anesthetized, animals are shaven and hair remover is applied to remove all traces of fur from the chest area. The chest area is further prepped with 70% ETOH and ultrasound gel is applied. Using a GE System Vingmed ultrasound system (General Electric Medical Systems), a 10 MHz probe is placed on the chest wall and images are acquired in the short axis view at the level of the papillary muscles. 2-D M-mode images of the left ventricle are taken prior to, and after, compound bolus injection or infusion. In vivo fractional shortening ((end diastolic diameter−end systolic diameter)/end diastolic diameter×100) is determined by analysis of the M-mode images using the GE EchoPak software program.

C. Bolus and Infusion Efficacy For bolus and infusion protocols, fractional shortening is determined using echocardiography as described above. For bolus and infusion protocols, five pre-dose M-Mode images are taken at 30 second intervals prior to bolus injection or infusion of compounds. After injection, M-mode images are taken at 1 min and at five minute intervals thereafter up to 30 min. Bolus injection (0.5-5 mg/kg) or infusion is via a tail vein catheter. Infusion parameters are determined from pharmacokinetic profiles of the compounds. For infusion, animals received a 1 minute loading dose immediately followed by a 29 minute infusion dose via a tail vein catheter. The loading dose is calculated by determining the target concentration x the steady state volume of distribution. The maintenance dose concentration is determined by taking the target concentration x the clearance. Compounds are formulated in 25% cavitron vehicle for bolus and infusion protocols. Blood samples are taken to determine the plasma concentration of the compounds.

Example 11

Hemodynamics in Normal and Heart Failure Animals

Animals are anesthetized with isoflurane, maintained within a surgical plane, and then shaven in preparation for catheterization. An incision is made in the neck region and the right carotid artery cleared and isolated. A 2 French Millar Micro-tip Pressure Catheter (Millar Instruments, Houston, Tex.) is cannulated into the right carotid artery and threaded past the aorta and into the left ventricle. End diastolic pressure readings, max±dp/dt, systolic pressures and heart rate are determined continuously while compound or vehicle is infused. Measurements are recorded and analyzed using a PowerLab and the Chart 4 software program (ADInstruments, Mountain View, Calif.). Hemodynamics measurements are performed at a select infusion concentration. Blood samples are taken to determine the plasma concentration of the compounds.

Example 12

Left Coronary Artery Occlusion Model of Congestive Heart Failure

A. Animals Male Sprague-Dawley CD (220-225 g; Charles River) rats are used in this experiment. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study. The animals are fasted overnight prior to surgery.

B. Occlusion Procedure Animals are anaesthetized with ketamine/xylazine (95 mg/kg and 5 mg/kg) and intubated with a 14-16-gauge modified intravenous catheter. Anesthesia level is checked by toe pinch. Core body temperature is maintained at 37° C. by using a heating blanket. The surgical area is clipped and scrubbed. The animal is placed in right lateral recumbency and initially placed on a ventilator with a peak inspiratory pressure of 10-15 cm $H_2O$ and respiratory rate 60-110 breaths/min. 100% $O_2$ is delivered to the animals by the ventilator. The surgical site is scrubbed with surgical scrub and alcohol. An incision is made over the rib cage at the $4^{th}$-$5^{th}$ intercostal space. The underlying muscles are dissected with care to avoid the lateral thoracic vein, to expose the intercostal muscles. The chest cavity is entered through $4^{th}$-$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage.

The left coronary artery is occluded by tying the suture around the artery ("LCO"). Sham animals are treated the same, except that the suture is not tied. The incision is closed in three layers. The rat is ventilated until able to ventilate on its own. The rats are extubated and allowed to recover on a heating pad. Animals receive buprenorphine (0.01-0.05 mg/kg SQ) for post operative analgesia. Once awake, they are returned to their cage. Animals are monitored daily for signs of infection or distress. Infected or moribund animals are euthanized. Animals are weighed once a week.

C. Efficacy Analysis Approximately eight weeks after infarction surgery, rats are scanned for signs of myocardial infarction using echocardiography. Only those animals with decreased fractional shortening compared to sham rats are utilized further in efficacy experiments. In all experiments, there are four groups, sham+vehicle, sham+compound, LCL+vehicle and LCL+compound. At 10-12 weeks post LCL, rats are infused at a select infusion concentration. As before, five pre-dose M-Mode images are taken at 30 second intervals prior to infusion of compounds and M-mode images are taken at 30 second intervals up to 10 minutes and every minute or at five minute intervals thereafter. Fractional shortening is determined from the M-mode images. Comparisons between the pre-dose fractional shortening and compound treatment are performed by ANOVA and a post-hoc Student—Newman-Keuls. Animals are allowed to recover and within 7-10 days, animals are again infused with compounds using the hemodynamic protocol to determine hemodynamic changes of the compounds in heart failure animals. At the end to the infusion, rats are killed and the heart weights determined.

When tested as described in Examples above, compounds of Formula I are shown to have the desired activity.

Example 13

Cardiac Contractility in vitro and in vivo in a Rat Model of Heart Failure

A myofibril assay is used to identify compounds (myosin activators) that directly activate the cardiac myosin ATPase. The cellular mechanism of action, in vivo cardiac function in Sprague Dawley (SD) rats, and efficacy in SD rats with defined heart failure to active compound is then determined. Cellular contractility was quantified using an edge detection strategy and calcium transient measured using fura-2 loaded adult rat cardiac myocytes. Cellular contractility increased over baseline within 5 minutes of exposure to an active compound (0.2 μM) without altering the calcium transient. Combination of active compound with isoproterenol (β-adrenergic agonist) should result only in an additive increase in contractility with no further change in the calcium transient demonstrating the active compound was not inhibiting the PDE pathway. In vivo contractile function in anesthetized SD rats is quantified using echocardiography (M-mode) and simultaneous pressure measurements. SD rats are infused with vehicle or active compound at 0.25-2.5 mg/kg/hr. The active compound should increase fractional shortening (FS) and ejection fraction (EF) in a dose-dependent manner with no significant change in peripheral blood pressures or heart rate except at the highest dose. Rats with defined heart failure induced by left coronary ligation, or sham treated rats may have similar and significant increases in FS and EF when treated with 0.7-1.2 mg/kg/hr active compound. In summary, the active compound increased cardiac contractility without increasing the calcium transient and was efficacious in a rat model of heart failure, indicating the active compound may be a useful therapeutic in the treatment of human heart failure.

Example 14

Pharmacology

The pharmacology of at least one chemical entity described herein is investigated in isolated adult rat cardiac myocytes, anesthetized rats, and in a chronically instrumented canine model of heart failure induced by myocardial infarction combined with rapid ventricular pacing. The active compound increases cardiac myocyte contractility (EC20=0.2 μM) but does not increase the magnitude or change the kinetics of the calcium transient at concentrations up to 10 μM in Fura-2 loaded myocytes. The active compound (30 μM) does not inhibit phosphodiesterase type 3.

In anesthetized rats, the active compound increases echocardiographic fractional shortening from 45±5.1% to 56±4.6% after a 30 minute infusion at 1.5 mg/kg/hr (n=6, p <0.01).

In conscious dogs with heart failure, the active compound (0.5 mg/kg bolus, then 0.5 mg/kg/hr i.v. for 6-8 hours) increases fractional shortening by 74±7%, cardiac output by 45±9%, and stroke volume by 101±19%. Heart rate decreases by 27±4% and left atrial pressure falls from 22±2 mmHg to 10±2 mmHg (p <0.05 for all). In addition, neither mean arterial pressure nor coronary blood flow changes significantly. Diastolic function is not impaired at this dose. There are no significant changes in a vehicle treated group. The active compound improved cardiac function in a manner that suggests that compounds of this class may be beneficial in patients with heart failure.

Example 15

Pharmaceutical Composition

A pharmaceutical composition for intravenous administration is prepared in the following manner.

1 mg/mL (as free base) IV solution with the vehicle being 50 mM citric acid, pH adjusted to 5.0 with NaOH:

| Composition | Unit Formula (mg/mL) |
| --- | --- |
| Active Agent | 1.00 |
| Citric Acid | 10.51 |
| Sodium Hydroxide | qs to pH 5.0 |
| Water for Injection (WFI) | q.s. to 1 mL |

*All components other than the active compound are USP/Ph. Eur. compliant

A suitable compounding vessel is filled with WFI to approximately 5% of the bulk solution volume. The citric acid (10.51 g) is weighed, added to the compounding vessel and stirred to produce 1 M citric acid. The active agent (1.00 g) is weighed and dissolved in the 1 M citric acid solution. The resulting solution is transferred to a larger suitable compounding vessel and WFI is added to approximately 85% of the bulk solution volume. The pH of the bulk solution is measured and adjusted to 5.0 with 1 N NaOH. The solution is brought to its final volume (1 liter) with WFI.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound chosen from
tert-butyl 4-{[3-({[(6-methyl-3-pyridyl)amino]carbonylamino}methyl)phenyl]methyl}-piperazinecarboxylate;
methyl 4-{[3-({[(6-methyl-3-pyridyl)amino]carbonylamino}methyl)phenyl]methyl}-piperazinecarboxylate;
N-[(3-{[4-(ethylsulfonyl)piperazinyl]methyl}phenyl)methyl][(6-methyl(3-pyridyl))amino]carboxamide;
N-({3-[(4-acetylpiperazinyl)methyl]phenyl}methyl)[(6-methyl(3-pyridyl))amino]carboxamide;
N-{[3-({4-[(dimethylamino)sulfonyl]piperazinyl}methyl)phenyl]methyl}[(6-methyl(3-pyridyl))amino]carboxamide;
tert-butyl 4-{[4-fluoro-3-({[(6-methyl(3-pyridyl))amino]carbonylamino}methyl)phenyl]methyl}piperazinecarboxylate;
methyl 4-{[4-fluoro-3-({[(6-methyl(3-pyridyl))amino]carbonylamino}methyl)phenyl]methyl}piperazinecarboxylate;
ethyl 4-{[4-fluoro-3-({[(6-methyl(3-pyridyl))amino]carbonylamino}methyl)phenyl]methyl}piperazinecarboxylate;
N-({5-[(4-acetylpiperazinyl)methyl]-2-fluorophenyl}methyl)[(6-methyl(3-pyridyl))amino]carboxamide;
N-[(5-{[4-(N,N-dimethylcarbamoyl)piperazinyl]methyl}-2-fluorophenyl)methyl][(6-methyl(3-pyridyl))amino]carboxamide;
N-[(5-{[4-(ethylsulfonyl)piperazinyl]methyl}-2-fluorophenyl)methyl][(6-methyl(3-pyridyl))amino]carboxamide;
N-{[5-({4-[(dimethylamino)sulfonyl]piperazinyl}methyl)-2-fluorophenyl]methyl}[(6-methyl(3-pyridyl))amino]carboxamide;
methyl 4-{[2-fluoro-3-({[(6-methyl(3-pyridyl))amino]carbonylamino}methyl)phenyl]methyl}piperazinecarboxylate;
N-[(3-{[4-(ethylsulfonyl)piperazinyl]methyl}-5-fluorophenyl)methyl][(6-methyl(3-pyridyl))amino]carboxamide;
methyl 4-{[2-chloro-5-({[(6-methyl(3-pyridyl))amino]carbonylamino}methyl)phenyl]methyl}piperazinecarboxylate;
N-[(4-chloro-3-{[4-(ethylsulfonyl)piperazinyl]methyl}phenyl)methyl][(6-methyl(3-pyridyl))amino]carboxamide;
N-{[3-({4-[(dimethylamino)sulfonyl]piperazinyl}methyl)-4-chlorophenyl]methyl}[(6-methyl(3-pyridyl))amino]carboxamide;
N-[(3-{[4-(N,N-dimethylcarbamoyl)piperazinyl]methyl}-4-chlorophenyl)methyl][(6-methyl(3-pyridyl))amino]carboxamide;
N-({3-[(4-acetylpiperazinyl)methyl]-4-chlorophenyl}methyl)[(6-methyl(3-pyridyl))amino]carboxamide;
N-({4-chloro-3-[(4-cyanopiperazinyl)methyl]phenyl}methyl)[(6-methyl(3-pyridyl))amino]carboxamide;
methyl 4-{[2-fluoro-5-({[(6-methyl(3-pyridyl))amino]carbonylamino}methyl)phenyl]methyl}piperazinecarboxylate;
N-({3-[(4-acetylpiperazinyl)methyl]-4-fluorophenyl}methyl)[(6-methyl(3-pyridyl))amino]carboxamide;
N-[(3-{[4-(ethylsulfonyl)piperazinyl]methyl}-4-fluorophenyl)methyl][(6-methyl(3-pyridyl))amino]carboxamide;
N-[(3-{[4-(N,N-dimethylcarbamoyl)piperazinyl]methyl}-4-fluorophenyl)methyl][(6-methyl(3-pyridyl))amino]carboxamide;
N-{[3-({4-[(dimethylamino)sulfonyl]piperazinyl}methyl)-4-fluorophenyl]methyl}[(6-methyl(3-pyridyl))amino]carboxamide;
N-{[3-({4-[(dimethylamino)sulfonyl]piperazinyl}methyl)-5-chlorophenyl]methyl}[(6-methyl(3-pyridyl))amino]carboxamide;
N-({5-chloro-3-[(4-cyanopiperazinyl)methyl]phenyl}methyl)[(6-methyl(3-pyridyl))amino]carboxamide;
N-[(3-{[4-(ethylsulfonyl)piperazinyl]methyl}-5-methylphenyl)methyl][(6-methyl(3-pyridyl))amino]carboxamide;
N-({3-[(4-acetylpiperazinyl)methyl]-5-methylphenyl}methyl)[(6-methyl(3-pyridyl))amino]carboxamide;
N-{[3-({4-[(dimethylamino)sulfonyl]piperazinyl}methyl)-5-methylphenyl]methyl}[(6-methyl(3-pyridyl))amino]carboxamide;
N-[(3-{[4-(ethylsulfonyl)piperazinyl]methyl}-4-methylphenyl)methyl][(6-methyl(3-pyridyl))amino]carboxamide;
N-{[3-({4-[(dimethylamino)sulfonyl]piperazinyl}methyl)-4-methylphenyl]methyl}[(6-methyl(3-pyridyl))amino]carboxamide;
N-({3-[(4-acetylpiperazinyl)methyl]-4-methylphenyl}methyl)[(6-methyl(3-pyridyl))amino]carboxamide;
methyl 4-{[4-(difluoromethoxy)-3-({[(6-methyl(3-pyridyl))amino]carbonylamino}-methyl)phenyl]methyl}piperazinecarboxylate;
ethyl 4-{[4-(difluoromethoxy)-3-({[(6-methyl(3-pyridyl))amino]carbonylamino}-methyl)phenyl]methyl}piperazinecarboxylate;
ethyl 4-{[3-({[(6-cyano(3-pyridyl))amino]carbonylamino}methyl)-4-fluorophenyl]methyl}piperazinecarboxylate;
methyl 4-{[2-methyl-5-({[(6-methyl(3-pyridyl))amino]carbonylamino}methyl)phenyl]methyl}piperazinecarboxylate;
ethyl 4-{[4-fluoro-3-({[(6-methoxy(3-pyridyl))amino]carbonylamino}methyl)phenyl]methyl}piperazinecarboxylate;
ethyl 4-[(4-fluoro-3-{[(pyrimidin-5-ylamino)carbonylamino]methyl}phenyl)methyl]-piperazinecarboxylate;
N-[(2-fluoro-5-{[4-(methylsulfonyl)piperazinyl]methyl}phenyl)methyl][(6-methyl(3-pyridyl))amino]carboxamide;
methylethyl 4-{[4-fluoro-3-({[(6-methyl(3-pyridyl))amino]carbonylamino}methyl)-phenyl]methyl}piperazinecarboxylate;
N-{[2-fluoro-5-({4-[(methylethyl)sulfonyl]piperazinyl}methyl)phenyl]methyl}[(6-methyl(3-pyridyl))amino]carboxamide;

N-[(2-fluoro-5-{[4-(3-methylbutanoyl)piperazinyl]methyl}phenyl)methyl][(6-methyl(3-pyridyl))amino]carboxamide;
N-[(2-fluoro-5-{[4-(propylsulfonyl)piperazinyl]methyl}phenyl)methyl][(6-methyl(3-pyridyl))amino]carboxamide;
N-[(5-{[4-(2,2-dimethyl propanoyl)piperazinyl]methyl}-2-fluorophenyl)methyl][(6-methyl(3-pyridyl))amino]carboxamide;
ethyl 4-{[2-(difluoromethoxy)-5-({[(6-methyl(3-pyridyl))amino]carbonylamino}-methyl)phenyl]methyl}piperazinecarboxylate;
N-[(4-(difluoromethoxy)-3-{[4-(ethylsulfonyl)piperazinyl]methyl}phenyl)methyl][(6-methyl(3-pyridyl))amino]carboxamide;
N-[(4-(difluoromethoxy)-3-{[4-(methylsulfonyl)piperazinyl]methyl}phenyl)methyl][(6-methyl(3-pyridyl))amino]carboxamide;
ethyl 4-{[4-fluoro-3-({[(3-methylisoxazol-5-yl)amino]carbonylamino}methyl)phenyl]methyl}piperazinecarboxylate;
ethyl 4-{[3-({[(6-acetyl(3-pyridyl))amino]carbonylamino}methyl)-4-fluorophenyl]methyl}piperazinecarboxylate;
methyl 4-{[4-methyl-3-({[(6-methyl(3-pyridyl))amino]carbonylamino}methyl)phenyl]methyl}piperazinecarboxylate;
ethyl 4-{[4-methyl-3-({[(6-methyl(3-pyridyl))amino]carbonylamino}methyl)phenyl]methyl}piperazinecarboxylate;
methylethyl 4-{[4-methyl-3-({[(6-methyl(3-pyridyl))amino]carbonylamino}methyl)-phenyl]methyl}piperazinecarboxylate;
N-[(5-{[4-(ethylsulfonyl)piperazinyl]methyl}-2-methylphenyl)methyl][(6-methyl(3-pyridyl))amino]carboxamide;
N-({5-[(4-acetylpiperazinyl)methyl]-2-methylphenyl}methyl)[(6-methyl(3-pyridyl))amino]carboxamide;
[(6-methyl(3-pyridyl))amino]-N-[(2-methyl-5-{[4-(methylsulfonyl)piperazinyl]-methyl}phenyl)methyl]carboxamide;
[(6-methyl(3-pyridyl))amino]-N-{[2-methyl-5-({4-[(methylethyl)sulfonyl]piperazinyl}-methyl)phenyl]methyl}carboxamide;
[(6-methyl(3-pyridyl))amino]-N-[(2-methyl-5-{[4-(2-methylpropanoyl)piperazinyl]-methyl}phenyl)methyl]carboxamide;
tert-butyl 4-{[2,4-difluoro-3-({[(6-methyl(3-pyridyl))amino]carbonylamino}-methyl)phenyl]methyl}piperazinecarboxylate;
methyl 4-{[2,4-difluoro-3-({[(6-methyl(3-pyridyl))amino]carbonylamino}-methyl)phenyl]methyl}piperazinecarboxylate;
ethyl 4-{[2,4-difluoro-3-({[(6-methyl(3-pyridyl))amino]carbonylamino}-methyl)phenyl]methyl}piperazinecarboxylate;
N-({3-[(4-acetylpiperazinyl)methyl]-2,6-difluorophenyl}methyl)[(6-methyl(3-pyridyl))amino]carboxamide;
N-[(2,6-difluoro-3-{[4-(methylsulfonyl)piperazinyl]methyl}phenyl)methyl][(6-methyl(3-pyridyl))amino]carboxamide;
N-[(3-{[4-(ethylsulfonyl)piperazinyl]methyl}-2,6-difluorophenyl)methyl][(6-methyl(3-pyridyl))amino]carboxamide;
N-{[3-({4-[(dimethylamino)sulfonyl]piperazinyl}methyl)-2,6-difluorophenyl]methyl}[(6-methyl(3-pyridyl))amino]carboxamide;
[(6-cyano(3-pyridyl))amino]-N-[(5-{[4-(ethylsulfonyl)piperazinyl]methyl}-2-fluorophenyl)methyl]carboxamide;
[(6-acetyl(3-pyridyl))amino]-N-[(5-{[4-(ethylsulfonyl)piperazinyl]methyl}-2-fluorophenyl)methyl]carboxamide;
ethyl 4-{[4-fluoro-3-({[(2-methylpyrimidin-5-yl)amino]carbonylamino}methyl)phenyl]-methyl}piperazinecarboxylate;
N-[(5-{[4-(ethylsulfonyl)piperazinyl]methyl}-2-fluorophenyl)methyl][(6-methoxy(3-pyridyl))amino]carboxamide;
N-[(5-{[4-(ethylsulfonyl)piperazinyl]methyl}-2-fluorophenyl)methyl](pyrimidin-5-ylamino)carboxamide;
tert-butyl 4-{[4-chloro-3-({[(6-methyl(3-pyridyl))amino]carbonylamino}methyl)phenyl]-methyl}piperazinecarboxylate;
N-[(5-{[4-(ethylsulfonyl)piperazinyl]methyl}-2-fluorophenyl)methyl][(2-methylpyrimidin-5-yl)amino]carboxamide;
N-{[2-chloro-5-(piperazinylmethyl)phenyl]methyl}[(6-methyl(3-pyridyl))amino]carboxamide;
methyl 4-{[4-chloro-3-({[(6-methyl(3-pyridyl))amino]carbonylamino}methyl)-phenyl]methyl}piperazinecarboxylate;
N-[(2-chloro-5-{[4-(methylsulfonyl)piperazinyl]methyl}phenyl)methyl][(6-methyl(3-pyridyl))amino]carboxamide;
N-[(2-chloro-5-{[4-(ethylsulfonyl)piperazinyl]methyl}phenyl)methyl][(6-methyl(3-pyridyl))amino]carboxamide;
N-{[4-({4-[(dimethylamino)sulfonyl]piperazinyl}methyl)phenyl]methyl}[(6-methyl(3-pyridyl))amino]carboxamide;
N-[(5-{[4-(ethylsulfonyl)piperazinyl]methyl}-2-fluorophenyl)methyl][(6-methoxy(3-pyridyl))amino]carboxamide; and
N-[(5-{[4-(ethylsulfonyl)piperazinyl]methyl}-2-fluorophenyl)methyl][(6-methyl(3-pyridyl))amino]carboxamide,
or a pharmaceutically acceptable salt thereof.

2. A pharmaceutical composition comprising a pharmaceutically acceptable excipient and a compound of claim 1, or a pharmaceutically acceptable salt thereof.

3. A pharmaceutical composition of claim 2, wherein the composition is formulated in a form chosen from injectable fluids, aerosols, tablets, pills, capsules, syrups, creams, gels, and transdermal patches.

* * * * *